United States Patent [19]
Hawley et al.

[11] Patent Number: 5,858,963
[45] Date of Patent: Jan. 12, 1999

[54] INDUCING XENOGRAFT TOLERANCE AND PORCINE CYTOKINES THEREFOR

[75] Inventors: Robert J. Hawley, Newton; Rodney L. Monroy, Rockport; Margaret D. Rosa, Winchester, all of Mass.; Bernice Z. Schacter, Madison, Conn.; Paul D. Ronath, Boston, Mass.

[73] Assignee: BioTransplant, Inc., Charlestown, Mass.

[21] Appl. No.: 436,890

[22] Filed: May 8, 1995

Related U.S. Application Data

[60] Division of Ser. No. 133,979, Oct. 8, 1993, Pat. No. 5,589,582, which is a continuation-in-part of Ser. No. 967,188, Oct. 27, 1992, abandoned.

[51] Int. Cl.$^6$ .......................... A61K 38/00; A01N 37/18
[52] U.S. Cl. .......................... 514/2; 424/93.2; 424/93.1; 424/85.1; 435/240.2
[58] Field of Search .................. 424/93.1, 93.2, 424/85.1; 435/240.2; 514/2

[56] References Cited

PUBLICATIONS

Sykes et al. "Xenograft Tolerance," Immunological Reviews, vol. 141: 213–244, Oct. 1994.
Sablinski et al., *Xenotransplantation*, 2:264–270 (1995).
Giovino et al., Porcine Specific Cytokines Enhance Porcine Bone Marrow Engraftment and Survival in a Xenogeneic Stromal Environment (Abstract), 3rd International Congress for Xenotransplantation, Boston, Oct. 1995.
Sablinski et al., Long Term Discordant Xenogeneic (Porcine To Primate) Bone Marrow Chimerism in a Monkey Treated With Porcine–Specific Stem Cell Factor and IL–3 (Abstract), 3rd International Congress for Xenotransplantation, Boston, Oct. 1995.
Yang et al., Enhanced Xenogeneic Hematopoietic Chimerism In Mice Receiving Porcine Donor–Specific Growth Factors (Abstract), 3rd International Congress for Xenotransplantation, Boston, Oct. 1995.

*Primary Examiner*—Jasemine C. Chambers
*Assistant Examiner*—Karen M. Hauda
*Attorney, Agent, or Firm*—Elliot M. Olstein; Raymond J. Lillie

[57] ABSTRACT

A method of enhancing tolerance of a porcine transplant in a xenogeneic recipient by administering porcine bone marrow cells to the recipient and of enhancing proliferation and engraftment of the porcine bone marrow cells by exposing said cells to at least one substantially pure porcine cytokine and porcine cytokines that are substantially free of other porcine proteins and preferentially enhance the proliferation and engraftment of porcine bone marrow cells in the presence of bone marrow cells of other species. Protein and DNA sequence(s) for such porcine cytokines.

10 Claims, 19 Drawing Sheets

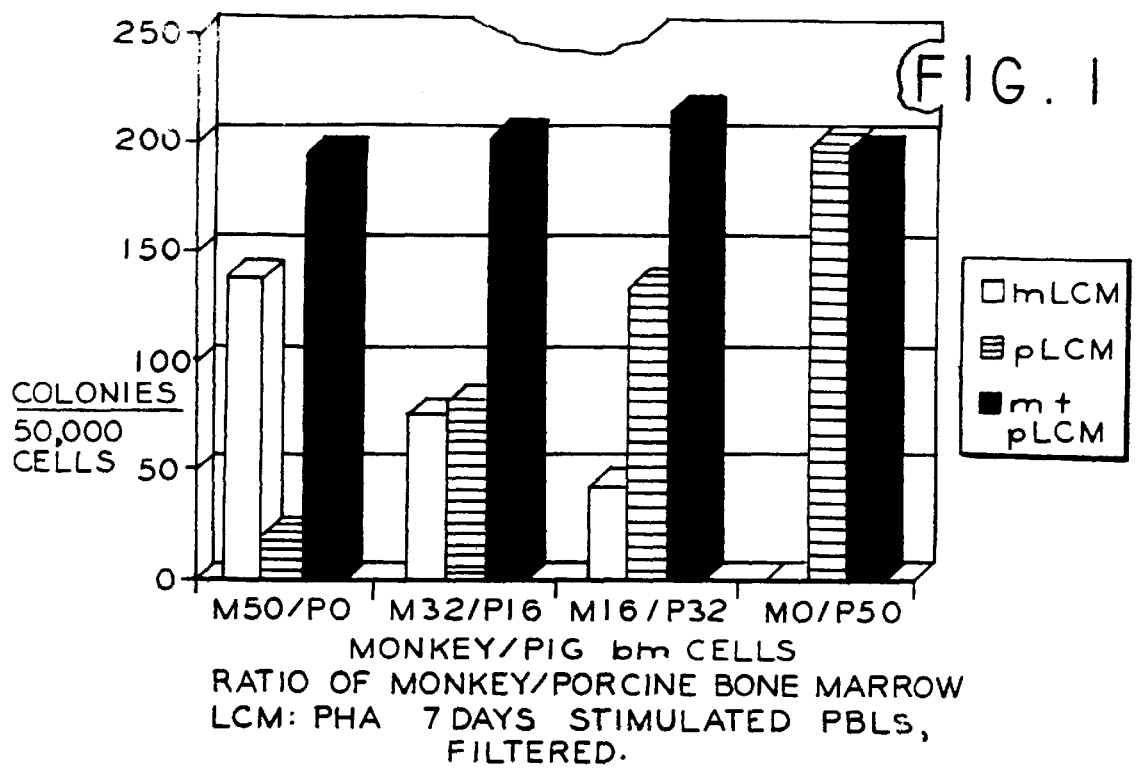
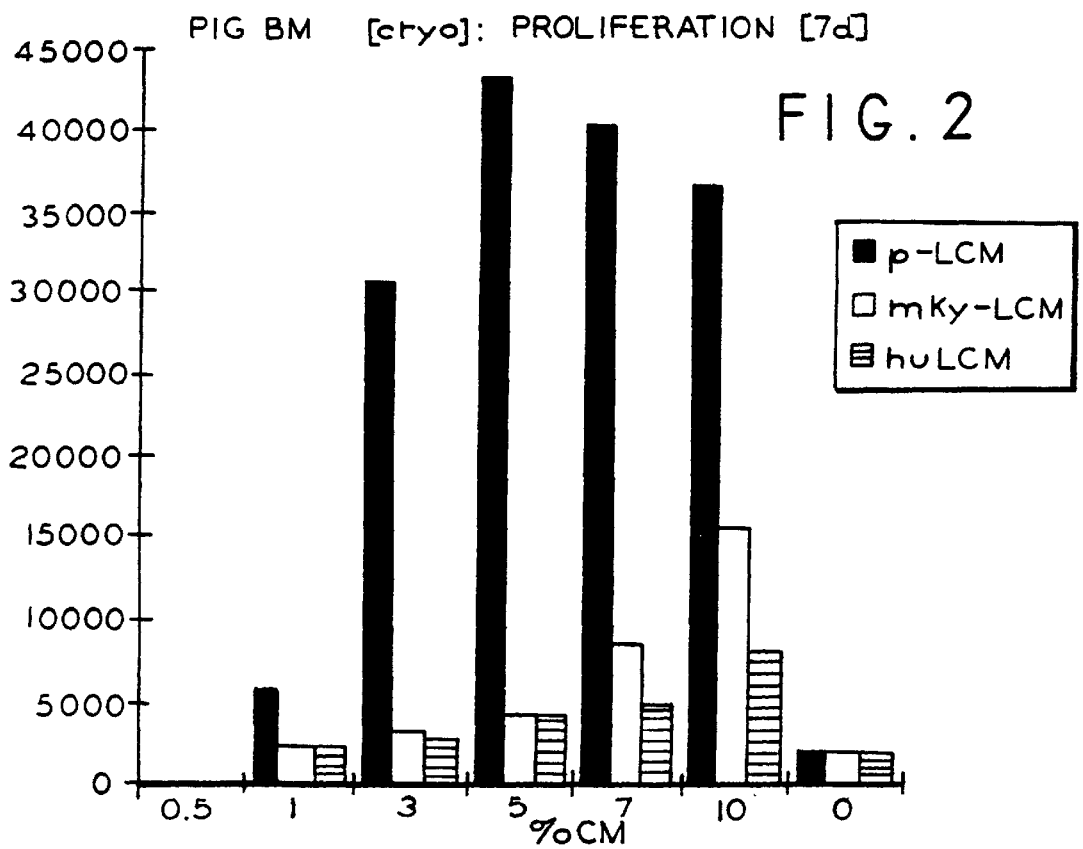

FIG. 3A

CHEF-3 SEQUENCE

```
                                                       GCGCT GCCTTCCTT    15

ATG AAG AAG ACA CAA ACT TGG ATT ATC ACT TGC ATT TAT CTT CAA CTG           63
Met Lys Lys Thr Gln Thr Trp Ile Ile Thr Cys Ile Tyr Leu Gln Leu
-25                 -20                 -15                 -10

CTC CTA TTT AAT CCT CTC GTC AGA ACT CAA GGG ATC TGC AGG AAC CGT          111
Leu Leu Phe Asn Pro Leu Val Arg Thr Gln Gly Ile Cys Arg Asn Arg
        -5                                   1

GTG ACT GAT GAT GTG AAA GAC GTT ACA AAA TTG GTG GCA AAT CTT CCA          159
Val Thr Asp Asp Val Lys Asp Val Thr Lys Leu Val Ala Asn Leu Pro
            10                  15                  20

AAA GAC TAT AAG ATA ACC CTC AAA TAT GTC CCC GGG ATG GAC GTT TTG          207
Lys Asp Tyr Lys Ile Thr Leu Lys Tyr Val Pro Gly Met Asp Val Leu
        25                  30                  35

CCT AGT CAT TGT TGG ATA AGC GAA ATG GTG GAA CAA CTG TCA GTC AGC          255
Pro Ser His Cys Trp Ile Ser Glu Met Val Glu Gln Leu Ser Val Ser
40                  45                  50                  55

TTG ACT GAT CTT CTG GAC AAG TTT TCC AAT ATT TCT GAA GGC TTG AGT          303
Leu Thr Asp Leu Leu Asp Lys Phe Ser Asn Ile Ser Glu Gly Leu Ser
            60                  65                  70
```

MATCH WITH FIG. 3B

MATCH WITH FIG. 3A

```
AAT TAT TCT ATC ATA GAC AAA CTT GTG AAA ATT GTT GAT GAC CTC GTG   351
Asn Tyr Ser Ile Ile Asp Lys Leu Val Lys Ile Val Asp Asp Leu Val
         75                      80                      85

GAA TGC ATG GAA GAA CAC TCA TTT GAG AAT GTA AGA AAA TCA TCT AAG   399
Glu Cys Met Glu Glu His Ser Phe Glu Asn Val Arg Lys Ser Ser Lys
         90                      95                     100

AGC CCA GAA CCC AGG CTG TTT ACT CCT GAA AAA TTC TTT GGG ATT TTT   447
Ser Pro Glu Pro Arg Leu Phe Thr Pro Glu Lys Phe Phe Gly Ile Phe
        105                     110                     115

AAT AGA TCC ATC GAT GCC TTC AAG GAT TTG GAG ATG GTG GCA CCT AAA   495
Asn Arg Ser Ile Asp Ala Phe Lys Asp Leu Glu Met Val Ala Pro Lys
        120                     125                     130                135

ACT AGT GAA TGT GTG ATT TCT TCA ACA TTA ACT CCT GAA AAA GAT TCC   543
Thr Ser Glu Cys Val Ile Ser Ser Thr Leu Thr Pro Glu Lys Asp Ser
        140                     145                     150

AGA GTC AGT GTC ACA AAA CCA TTT ATG TTA CCC CCT GTT GCA GCC AGC   591
Arg Val Ser Val Thr Lys Pro Phe Met Leu Pro Pro Val Ala Ala Ser
        155                     160                     165

TCC CTT AGG AAT GAC AGC AGT AGC AGT AAT AGG AAA GCC TAA           633
Ser Leu Arg Asn Asp Ser Ser Ser Ser Asn Arg Lys Ala
        170                     175                     180
```

CHEF-2 SEQUENCE

GGCCGCTAA AGGCTAAAGT CCTCAGAAGG ATG TGG CTG CAG AAC CTG CTC CTG    56
                                 Met Trp Leu Gln Asn Leu Leu Leu
                                  1                          -10

GGC ACT GTG GTC TGC AGC ATC TCC GCT CCC ACC CGC CCA CCC AGC CCT    104
Gly Thr Val Val Cys Ser Ile Ser Ala Pro Thr Arg Pro Pro Ser Pro
              -5                    1                        5

GTC ACC CGG CCC TGG CAG CAT GTG GAT GCC ATC AAA GAA GCC CTG AGC    152
Val Thr Arg Pro Trp Gln His Val Asp Ala Ile Lys Glu Ala Leu Ser
          10                  15                  20

CTT CTA AAC AAC AGT AAT GAC ACA GCG GCT GTG ATG AAT GAA ACC GTA    200
Leu Leu Asn Asn Ser Asn Asp Thr Ala Ala Val Met Asn Glu Thr Val
 25                  30                  35                  40

GAC GTC GTC TGT GAA ATG TTT GAC CCC CAG GAG CCG ACA TGC GTG CAG    248
Asp Val Val Cys Glu Met Phe Asp Pro Gln Glu Pro Thr Cys Val Gln
              45                  50                  55

ACT CGC CTG AAC CTG TAC AAG CAG GGC CTG CGG GGC AGC CTC ACT AGG    296
Thr Arg Leu Asn Leu Tyr Lys Gln Gly Leu Arg Gly Ser Leu Thr Arg
 60                  65                  70

CTC AAG AGC CCC TTG ACT CTG TTG GCC AAG CAC TAT GAG CAG CAC TGC    344
Leu Lys Ser Pro Leu Thr Leu Leu Ala Lys His Tyr Glu Gln His Cys
 75                  80                  85

MATCH WITH FIG. 8B

FIG. 8B

MATCH WITH FIG. 8A

```
CCC CTC ACC GAG GAA ACT TCC GAA ACC CAG TCT ATC ACC TTC AAA    392
Pro Leu Thr Glu Glu Thr Ser Cys Glu Thr Gln Ser Ile Thr Phe Lys
         90                      95                     100

AGT TTC AAA GAC AGT CTG AAC AAA TTT CTT TTT ACC ATC CCC TTT GAC    440
Ser Phe Lys Asp Ser Leu Asn Lys Phe Leu Phe Thr Ile Pro Phe Asp
     105                     110                     115         120

TGC TGG GGG CCA GTC AAA AAG TAA AGCAGCCTGC AGCAGCCAGA AGCCAGCCTT    494
Cys Trp Gly Pro Val Lys Lys
                125

GCCGCACGGA TTGCTCCCAC TGACAGAGCC AAACCAAACT CAGGATCTTC ACCGTGGAGG    554

GACCACTGGC TGGCCAAGGC TGTAATGGGG CACAGACTTG CCCTGGGCCA TGTTGACCCT    614

GATACAGGCC TGGCAGGGGA AATGGCAGAT GTTTTATACC GGCAGGGATT AGCAATATTT    674

ATTAACCTAT TTATGTATTT TAATATTTAT TTATTTATT ATCTATTTAT TTATTAAGC    734

TTGAACTTCA TATTTATTCA AGATGTTTTA CCATAATAAT AAATTATTTA AAATAGCGGC    794

CGCT 798
```

FIG. 12A

CHEF-1 SEQUENCE

```
GGA TCCATCGTAC CGGCCCAAAC ATG AGC AGC CTC CCC CTT ATG CAT CTG CTC   53
                           Met Ser Ser Leu Pro Leu Met His Leu Leu
                                   -20                          -15

CTG CTG CTC ACA CTC CAT GCT CCT CAG GCA CAG GGG ATG CCT ACC         101
Leu Leu Leu Thr Leu His Ala Pro Gln Ala Gln Gly Met Pro Thr
            -10                      -5                    1

ACA ACA CTC CAA CCT AAA AAC TAC CTT GCC ATG ATC CAG GAA ATT ACA     149
Thr Thr Leu Gln Pro Lys Asn Tyr Leu Ala Met Ile Gln Glu Ile Thr
         5                      10                     15

AGA AGC CTA GAG AAC CTA ACT GTG ACT TCA AAT AAA TCC TTG ACG TTG     197
Arg Ser Leu Glu Asn Leu Thr Val Thr Ser Asn Lys Ser Leu Thr Leu
        20                      25                     30      35

AAT GAG CTC GAA ACC CTG GTG GTG AAT AAC ACT CTT CTG AGA CCA AAC CTG 245
Asn Glu Leu Glu Thr Leu Val Asn Asn Thr Leu Leu Arg Pro Asn Leu
        40                      45                     50

GAA GCA TTC GTG ACA TTT GCT GAA AAC CAC TTA AAA AAT ATT TCA GGA     293
Glu Ala Phe Val Thr Phe Ala Glu Asn His Leu Lys Asn Ile Ser Gly
        55                      60                     65
```

MATCH WITH FIG. 12B

FIG. 12B

MATCH WITH FIG. 12A

```
ATC AAG AAA AAC CTT GAG AAA TTC CGG CCA ATC CTG CCC ACG TCT ATG    341
Ile Lys Lys Asn Leu Glu Lys Phe Arg Pro Ile Leu Pro Thr Ser Met
             70                      75                      80

TCC ACG GAA GAG CCA ATC TCT ATT GAG GAG GGC GAC CTT GGT GAT TTC    389
Ser Thr Glu Glu Pro Ile Ser Ile Glu Glu Gly Asp Leu Gly Asp Phe
         85                      90                      95

CGG GCG AAA CTG ATG GAG TAT CTG GTT GTC CTT AGA GAC TCT CTG AAA    437
Arg Ala Lys Leu Met Glu Tyr Leu Val Val Leu Arg Asp Ser Leu Lys
100                     105                     110             115

CCC ATG ATC ACA GAG CCC TAA AATCTGAAGT GTGAACTCCA GCTCTCTCTC       488
Pro Met Ile Thr Glu Pro
                120

TGGAGCCCTG GAACGTCAGG AACAGCAGAT CGTCCTAAGA TGCCGTGGACC GTCTCTCACA 548

CCATCCAGGA CTGACGTTTT CTCCTGTGGA GTCTGTTGAA TTGTTAACTA TCTAATCCCT  608

GAAATGTGCA GCCCCATTTG TCCTTTTGCG ATTAGGTTCT CATTTTTATT GTATTGAGGC  668

TATTTATTTA TGTATGTATT TATTATTAT CTTGTGCAAT GTGAAATGTA TTTACTTAAC   728

AGAGAAGCCA TGGCCCTGCTC CTTCTGAATG AG 760
```

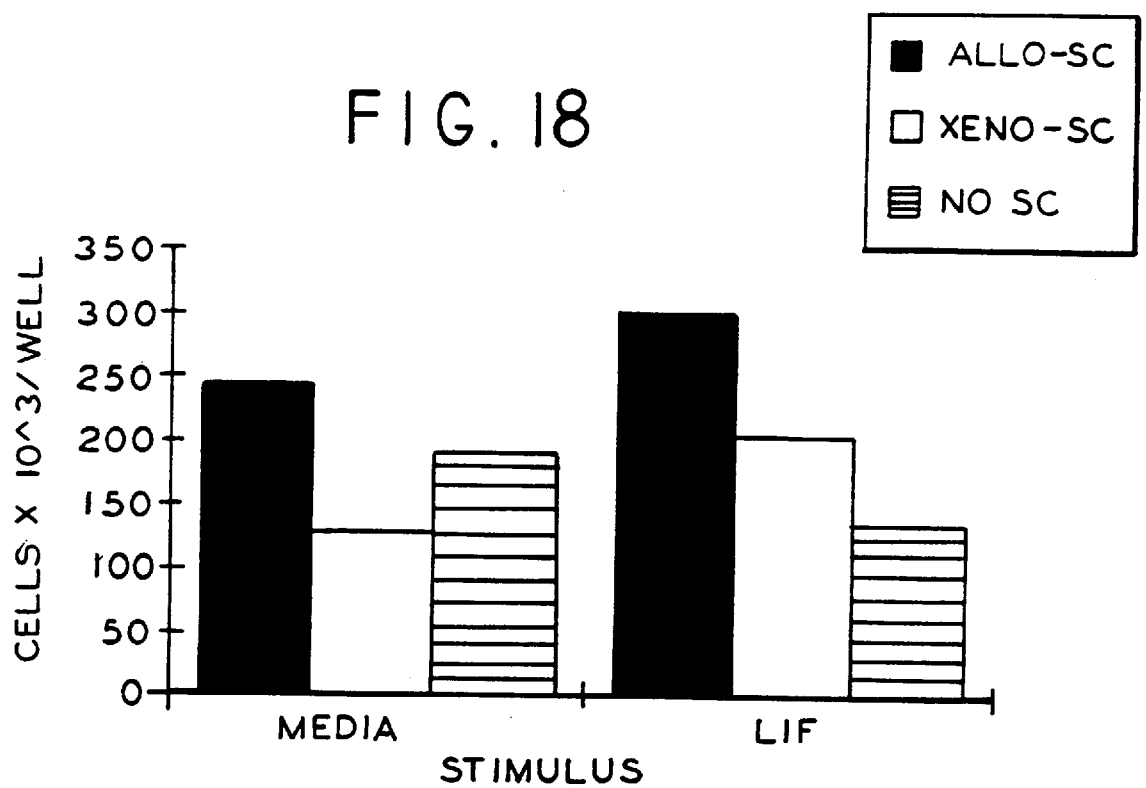
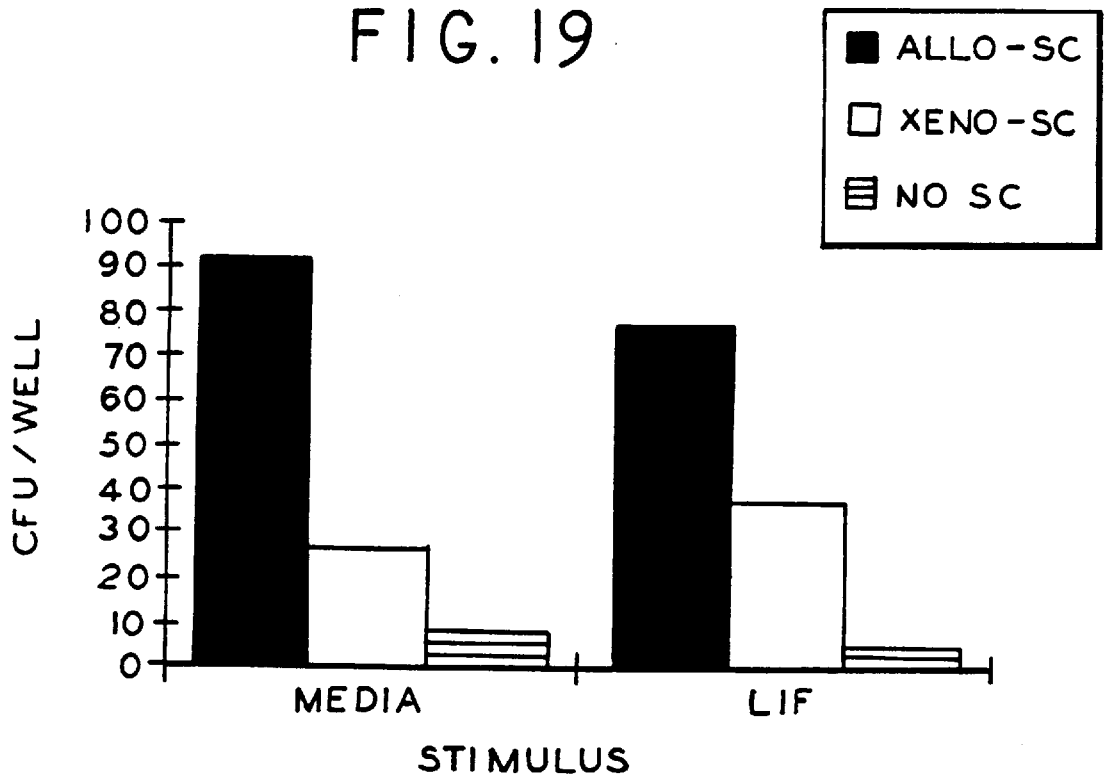

INDUCING XENOGRAFT TOLERANCE AND PORCINE CYTOKINES THEREFOR

This application is a divisional of application Ser. No. 08/133,979, filed Oct. 8, 1993, now U.S. Pat. No. 5,589,582, which is a continuation-in-part of U.S. Ser. No. 07/967,188, filed Oct. 27, 1992.

This invention relates to a method for enhancing xenogeneic transplantation of porcine tissue or organs using porcine bone marrow and porcine cytokines, and to recombinant DNA molecules for expression of porcine cytokines and fusion proteins containing them. The porcine cytokines are useful for improving engraftment, stabilization and proliferation of tissues, particularly bone marrow cells, in xenogeneic transplantation.

BACKGROUND OF THE INVENTION

Organ procurement currently poses one of the major problems in organ transplantation, as the number of patients requiring transplants far exceeds the number of organs available. Xenotransplantation may provide a solution to this problem. Phylogenetically, non-human primates are the most closely related species to humans and might therefore represent the first choice as donors. In 1969, Reetsma et al. achieved the first successful kidney human xenograft from a chimpanzee (Reetsma, K. et al., 1964, Ann. Surg. 160:384). However, the potential utilization of primate donors is limited by insufficient numbers, legal and ethical considerations, and the potential for transmitting dangerous viral diseases. Swine represent one of the few large animal species in which breeding characteristics make genetic experiments possible, making it possible to develop MHC homozygous lines of miniature swine. Miniature swine can be maintained at maximum adult weights of 200 to 300 lbs and are anatomically and physiologically close to humans. Therefore the organs of miniature swine seem appropriate for use as xenografts for human beings of all ages.

Tolerance to self major histocompatibility (MHC) antigens occurs during T cell maturation in the thymus (McDuffie et al., J. Immunol. 141:1840, 1988). Exposure of the immune system to MHC antigens during ontogeny can cause the immune system to lose reactivity to those antigens, thus leaving the animal specifically tolerant into adult life (Billingham et al., 1953, Nature 172:603). Transplantation immunologists have sought means of inducing tolerance in adult animals by production of lymphohematopoietic chimeras. The induction of tolerance across MHC barriers in adult mice by whole body irradiation (WBI) and bone marrow transplantation (BMT) has been studied extensively in murine models (Hayfield et al., 1983, Transplan. 36:183; Mayumi et al., 1989, J. Exp. Med. 169:213; Sykes et al., 1988, Immunol. Today 9:23).

The use of MHC mismatched BMT as a means of inducing tolerance to organ grafts can be accompanied by several major disadvantages: the preparative regimen involves lethal irradiation, with its inherent risks and toxicities; clinical applicability is limited by the fact that most potential recipients do not have an appropriate MHC-matched donor, and BMT across MHC barriers causes severe graft-vs-host-disease (GVHD). Removing the T lymphocytes in allogeneic bone marrow inocula (Rodt et al., 1971, Eur. J. Immunol. 4:25) to prevent GVHD is associated with increased rates of engraftment failure (Martin et al., 1988, Bone Marrow Transplant 3:445; O'Reilly et al., 1985, Transplant. Proc. 17:455; Soderling et al., 1985, J. Immunol., 135:941). While these drawbacks are generally considered acceptable for the treatment of otherwise lethal malignant diseases, they would severely limit the application of MHC mismatched BMT as a preparative regimen for organ transplantation, in which non-specific immunosuppressive agents, while not without major complications, are effective.

Use of a relatively non-toxic, non-myeloablative preparative regimen for bone marrow engraftment and specific transplantation tolerance has been applied to the concordant rat to mouse species combination (Sharabi, Y. et al., 1990, J. Exp. Med. 172:195–202). The treatment involved administration of monoclonal antibodies to eliminate mature T cell subsets (CD4 and CD8) as well as NK cells (NK1.1). These monoclonal antibodies permitted engraftment of xenogeneic bone marrow after only a sub-lethal (300 rads) dose of WBI and a local dose of 700 rads thymic irradiation. The -resulting lymphoid reconstitution was superior to that of previously mixed xenogeneic chimeras prepared by lethal irradiation and reconstitution with mixtures of T cell-depleted syngeneic and xenogeneic bone marrow (Sharabi, Y., et al., 1990, J. Exp. Med. 172:195–202; Ildstad, et al., 1984, Nature 307:168–170) as recipients did not suffer toxic effects from the preparative regimen. In addition, attempts have been made to lengthen the survival of skin allografts in primates and man by intravenously administering a polyclonal preparation of horse anti-human antithymocyte globulin (ATG). The ATG was injected simultaneously with and on days immediately following grafting (Cosimi, A. B. et al., 1970, Surgery. 68:54–61).

It has been recognized that the use of swine organs for xenogeneic transplantation to humans is facilitated by inducing tolerance (i.e., reducing the severity of and/or eliminating any immunological response to the transplant) to swine tissue using swine bone marrow. The swine bone marrow cells (BMC) can be transplanted to the recipient's marrow and engraft there. Engraftment, as used herein, refers to implantation or transplantation of porcine BMCs into a xenogeneic recipient or host such that the porcine BMCs proliferate, differentiate and function as bone marrow in the recipient. The porcine bone marrow can be introduced before transplantation of the swine organ, contemporaneously with the organ transplantation, or both. In this context, contemporaneously or substantially contemporaneously contemplates introduction during the same operative procedure or as part of preoperative preparation.

In accordance with the present invention, it has been recognized by the inventors that it would be highly desirable to promote the engraftment of the porcine bone marrow and that cytokines which have an effect on marrow engraftment are highly species specific in their effect. In accordance with the invention, the inventors recognized the deficiency that porcine cytokines effective to promote porcine bone marrow engraftment had not been identified, isolated, characterized or produced, such as by recombinant techniques and that such was highly desirable for use in the above and other applications.

Accordingly, other principal aspects of the invention are porcine cytokines that preferentially enhance the proliferation and engraftment of porcine bone marrow cells in the presence of bone marrow cells of other species, DNA sequences therefor and DNA molecules for expression of these porcine cytokines. More particularly, the invention provides porcine chimeric enhancement factors ("CHEFs") that are porcine analogs of interleukin-3 (hereinafter "CHEF-1"), granulocyte-macrophage colony stimulating factor (hereinafter "CHEF-2") and stem cell factor (hereinafter "CHEF-3") as well as combinations of these novel porcine cytokines with each other and with other porcine cytokines, such as porcine leukemia inhibitory factor (hereinafter "porcine LIF"). The porcine cytokines of the invention are contemplated to encompass the protein whether purified from native origin, expressed by recombinant methodologies or chemically synthesized.

As will be explained in more detail below, the porcine bone marrow that is preferentially stimulated by the porcine cytokines in the recipient prepares the recipient for the tissue or organ transplantation by inducing tolerance at both the B-cell and T-cell levels. Preferably, the bone marrow cells include immature cells (e.g., undifferentiated hematopoietic stem cells; these cells can be separated out of the bone marrow prior to administration), or a complex bone marrow sample including such cells can be used.

Preferred embodiments include those in which: swine of the same immunological profile are the donor of both the tissue or organ to be transplanted and the bone marrow; the recipient mammal is a primate, preferably a human; and the swine is a partially or completely inbred strain, e.g., a miniature swine. In a preferred embodiment of the method of use, the recipient is irradiated with low dose radiation prior to introducing the bone marrow, preferably with radiation of more than 100 rads and less than 400 rads.

BRIEF DESCRIPTION OF THE DRAWINGS

FIG. 1 graphically illustrates the extent of colony formation induced by mLCM, pLCM and their combination in various bone marrow cell populations of monkey, pig and mixed ratios of monkey/pig cells using LCM that was the spun, filtered supernatant of peripheral blood lymphocytes stimulated continuously for 7 days with PHA, based on the experiments reported in Example 1.

FIG. 2 graphically illustrates the dose dependence and exceptional species specificity of porcine bone marrow cell proliferation. Tritiated thymidine uptake (0–45,000 cpm) was measured using porcine, monkey and human LCM over a range of concentrations (V/V) of LCM in IMDM medium (% CM) in the experiments reported in Example 1.

FIG. 3 shows the nucleic acid sequence and derived amino acid sequence of the CHEF-3 coding region, as described in Examples 2, 3 and 4. Expression in mammalian cells begins with the first methionine, but signal peptide cleavage is predicted to yield a protein secreted from mammalian cells beginning with amino acid 26 (glutamine, indicated in bold).

FIG. 8 shows the nucleotide sequence and derived amino acid sequence of CHEF-2 determined by sequencing the cDNA insert of clone λNC1-1A and subclone pCHEF-2.pcd. Sequences derived from linkers used in construction of the cDNA library are underlined. Expression in mammalian cells starts at the first ATG (position 23, bold), beginning a typical mammalian signal peptide sequence, and continues to a TAA termination codon (position 462, bold), as described in Examples 5 and 6.

FIG. 12 shows the nucleotide sequence and derived amino acid sequence of pCHEF-1.pcd1, as described in Examples 8, 9 and 10. The first ATG (bold) starts at position 24, beginning a typical mammalian signal peptide, and continues to a TAA termination codon beginning at position 456 (bold). Underlined sequences indicate PCR primers ILP-F (positions 1–15, underlined) and ILP-R (positions 740–760, underlined) used to isolated the CHEF-1 cDNA by PCR.

FIGS. 16–23 illustrate results described in Example 11.

FIG. 16 graphically illustrates the results of the bone marrow cellular proliferation assay. Stimulation of pBMC by LIF (■) or a combination of CHEF-3 and LIF (20% CHEF; (□) is depicted in this Figure. Proliferation of porcine bone marrow cells is increased 2–3 fold by the stimulation with CHEF-3 and porcine LIF as compared to LIF alone.

FIG. 17 graphically illustrates the unique combined activities of CHEF-3 and LIF in a colony formation assay, where colony formation is assessed either in the presence of LIF alone (■) or with combinations of either 10% (□) or 20% CHEF-3 (♦).

FIGS. 18 and 19. Effect of LIF and either primary allo- or xeno-stromal cells on cellular and progenitor cell development of pBMC after 1 week in culture. The effect of LIF on pig bone marrow cellularity (FIG. 18) and progenitor cell content (FIG. 19) at the end of 7 days of culture on either pig stromal cells (■) or primate stromal cells (□) or no stromal cells (=). The results are mean values of 3 separate experiments.

FIGS. 20 and 21. Effect of LIF, CHEF 3 and either primary xeno or allo-stromal cells on cellularity (FIGS. 20A and 20B) and progenitor cell development (FIGS. 21A and 21B) after 1 week in culture. Cultures were established. The variable is the addition of either LIF [50ng/ml], CHEF-3 [20%COS cell supernatant] or the combination of both to standard LTBMC media. At the end of 7 days, all cells from 2 wells were harvested, cell number was determined and an aliquot of cells was plated in a colony forming assay.

Figure 4:
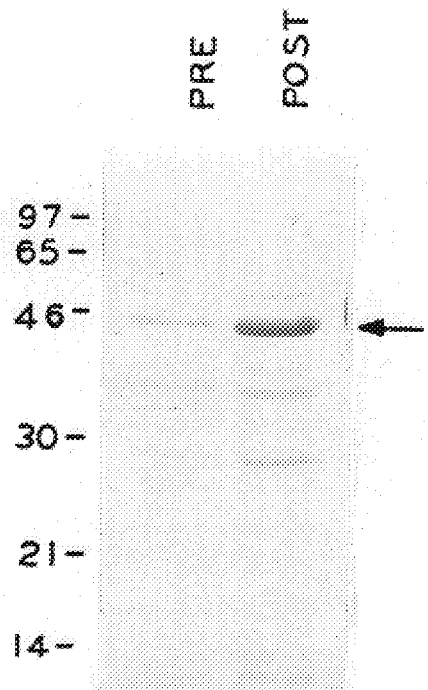
FIG. 4 shows an SDS-PAGE analysis of lysates of E. coli bearing plasmid pMDR1069, which encodes a GST-CHEF-3 fusion, as described in Example 3. Samples prior to induction with IPTG (PRE) and following a 5 hour induction with IPTG (POST) were analyzed with protein molecule weight markers indicated (in kDa). The induced GST-CHEF-3 fusion protein is indicated by the arrow.

A principal aspect of the invention relates to enhancing tolerance of a porcine transplant in a xenogeneic recipient, particularly a human, by administering to the recipient a tolerance-inducing amount of porcine bone marrow cells and at least one porcine cytokine in an amount sufficient to enhance the proliferation and engraftment of the porcine bone marrow cells therein. Porcine bone marrow cells and cytokines can be introduced to the xenogeneic recipient before and/or contemporaneously with introduction of the porcine transplant to the xenogeneic recipient. The porcine bone marrow cells are preferably administered systemically, e.g., intravenously.

The porcine cytokines can be selected to be those which preferentially enhance: activation of other porcine cytokines; proliferation of porcine marrow progenitor cells; proliferation of porcine marrow hematopoietic cells; proliferation of marrow stem (particularly hematopoietic stem) cells; or proliferation of porcine granulocyte and macrophage cells.

This can be accomplished, for example, by bathing the porcine bone marrow cells in a composition comprising at least one porcine cytokine in a physiologically acceptable liquid prior to their administration to the recipient. Also, the porcine cytokine(s) can be systemically administered to the recipient, e.g., by intravenous injection or infusion, in admixture with the porcine bone marrow cells or as a separately pharmaceutical preparation. When formulated as a separate preparation, the cytokine(s) are administered slightly before or substantially contemporaneously (as defined above) with the porcine bone marrow cells.

In another principal aspect, the invention relates to a porcine cytokine that is substantially free of other porcine proteins and preferentially enhances the proliferation and engraftment of porcine bone marrow cells in the presence of bone marrow cells of other species. Embodiments of this aspect include cytokine(s) isolated from native porcine tissue sources such as porcine tissue extracts, cultured cells and the like such that it is rendered substantially free of other proteins or macromolecules of porcine origin. Other embodiments include cytokine(s) prepared by recombinant techniques, including those using expression vectors in prokaryotic or eukaryotic host cells to form an expression system. The expression vectors can contain structural coding sequences for the cytokine that are fragments of cDNA prepared to be complementary to mRNA isolated from porcine cells or tissue extracts. Other embodiments include fusion protein products, of such expression systems, that exhibit similar porcine cytokine bone marrow proliferation and engraftment activities. Further embodiments include such proteins that are chemically synthesized as well as any proteins or fragments thereof that are substantially homologous. "Substantially homologous," which can refer both to nucleic acid and amino acid sequences, means that a particular subject sequence, for example, a mutant sequence, varies from a reference sequence by one or more substitutions, deletions, or additions, the net effect of which does not result in an adverse functional dissimilarity between reference and subject sequences. For purposes of the present invention, sequences having greater than 90 percent homology, equivalent biological activity, and equivalent expression characteristics are considered substantially homologous. For purposes of determining homology, truncation of the mature sequence should be disregarded. Sequences having lesser degrees of homology, comparable bioactivity, and equivalent expression characteristics are considered equivalents.

Definitions of certain additional terms used herein will provide guidance as to the contemplated metes and bounds of such terms. "Recombinant," as used herein, means that a protein is derived from recombinant (e.g., microbial or mammalian) expression systems. "rCHEF" means recombinant porcine cytokine chimeric enhancement factor "Microbial" refers to recombinant proteins made in bacterial or fungal (e.g., yeast) expression systems. As a product, "recombinant microbial" defines a porcine protein essentially free of native endogenous substances and unaccompanied by associated native glycosylation. Protein expressed in most bacterial cultures, e.g., E. coli, will be free of glycosylation modifications; protein expressed in yeast will have a glycosylation pattern different from that expressed in mammalian cells. "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, using a cloning vector. Such segments are provided in the form of an open reading frame uninterrupted by introns, which are typically present in eukaryotic genes. Sequences of non-translated DNA may be present downstream from the open reading frame, where they do not interfere with manipulation or expression of the coding regions. "Nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant "transcriptional unit," comprising regulatory elements derived from a microbial or viral operon.

"Recombinant expression vector" refers to a plasmid or phage comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

Generally, recombinant expression vectors will include origins of replication and selectable markers permitting transformation of the host cell, e.g., the ampicillin resistance gene of *E. coli* and the *S. cerevisiae* TRP1 gene, and a promoter derived from a highly-expressed gene to induce transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a porcine cytokine together with suitable translation initiation and termination signals in operable reading phase with a functional promoter. The vector will comprise one or more phenotypic selectable markers and an origin of replication to ensure amplification within the host. Suitable prokaryotic hosts for transformation include *E. coli, Bacillus subtilis, Salmonella typhimurium* and various species within the genera Pseudomonas, Streptomyces, and Staphylococcus, although others may, also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223–3 (Pharmacia Fine Chemicals, Uppsala, Sweden) and pGEM 1 (Promega, Madison, Wis., USA). These pBR322 "backbone" sections are combined with an appropriate promoter and the structural sequence to be expressed. Additional details regarding the use of a bacterial expression system to produce recombinant CHEF-3 protein as part of a fusion protein, with glutathione-S-transferase, are provided in Example 3, below.

Following transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation sites, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Additional details regarding the use of a mammalian high expression vectors to produce recombinant CHEF protein are provided in the working examples.

Recombinant protein produced in bacterial culture is usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of CHEF proteins can be disrupted by any convenient method, including freeze-thaw cycling, sonication, mechanical disruption, or use of cell lysing agents. Use of an expression system which expresses a CHEF protein as a secreted protein greatly simplifies purification.

"Recombinant expression system" means a substantially homogeneous monoculture of suitable host microorganisms, for example, bacteria such as *E. coli* or yeast such as *S. cerevisiae*, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA segment or synthetic gene to be expressed.

Mature porcine cytokines can be expressed in mammalian cells, yeast, bacteria, or other cells under the control of appropriate promoters. Cell-free translation systems can also be employed to produce porcine cytokines using RNAs derived from the DNA constructs of the present invention. Appropriate cloning and expression vectors for use with prokaryotic and eukaryotic hosts are described by *Maniatis, Molecular Cloning: A Laboratory Manual*, (Cold Spring Harbor, N.Y., 1985), the disclosure of which is hereby incorporated by reference.

One preferred embodiment of this aspect relates to porcine cytokine Chimerism Enhancing Factor-3 (CHEF-3) that has now been identified, isolated and prepared. The protein and DNA sequences of CHEF-3 and one possible coding sequence therefor are shown in the attached drawings and the method by which these were ascertained are described in the examples. The CHEF-3 porcine cytokine(s) of this aspect preferentially enhances the proliferation of porcine marrow progenitor cells, more particularly porcine marrow hematopoietic cells, stem cells and ideally porcine hematopoietic stem cells. The porcine cytokine referred to as "CHEF-3" herein has the polypeptide sequence shown as SEQ ID NO:4.

Another preferred embodiment of this aspect relates to porcine cytokine Chimerism Enhancing Factors (CHEFs), particularly CHEF-2 that has now been identified, isolated and prepared. The protein and DNA sequences of CHEF-2 and one possible coding sequence therefor are shown in the attached drawings and the method by which these were ascertained are described in the examples. The porcine cytokine(s) of this aspect preferentially enhances the proliferation of porcine granulocyte and macrophage cells. The porcine cytokine referred to as "CHEF-2" herein has the polypeptide sequence shown as SEQ ID NO:11.

Another preferred embodiment of this aspect relates to porcine cytokine Chimerism Enhancing Factors (CHEFs), particularly CHEF-1 that has now been identified, isolated and prepared. The protein and DNA sequences of CHEF-1 and one possible coding sequence therefor are shown in the attached drawings and the method by which these were ascertained are described in the examples. The porcine cytokine(s) of this aspect preferentially enhances the proliferation of porcine granulocyte and macrophage cells. The porcine cytokine referred to as "CHEF-1" herein has the polypeptide sequence shown as SEQ ID NO:21.

A plasmid (pCHEF-1.pcd1) containing the polynucleotide encoding CHEF-1, a plasmid (pCHEF-2.pcd) containing the polynucleotide encoding CHEF-2 and a plasmid (pCHEF-3) containing the polynucleotides encoding CHEF-3 were each deposited with the American Type Culture Collection, 12301 Parklawn Drive, Rockville, Md. 20852, on October 8, 1993. They were assigned ATCC Accession Numbers 75568, 75567 and 75569, respectively. Viability was confirmed on Oct. 14, 1993. Each deposit was made in compliance with the Budapest Treaty on the International Recognition of the Deposit of Microorganisms for the purposes of Patent Procedure.

Another preferred aspect of the invention relates to fusion proteins containing CHEF-3 and/or CHEF-2 and/or CHEF-1 activity and activity of at least one additional protein, particularly hematopoietic porcine cytokine activity, but also expression facilitating proteins, e.g. glutathione-S-transferase as in Example 2 that can be cleaved, e.g. by thrombin, for isolation of the CHEF protein.

Another aspect of the invention relates to combinations of CHEF-3 and/or CHEF-2 and/or CHEF-1 with other porcine cytokines when they are also substantially free of other porcine source proteins or other porcine native source macromolecules except for the CHEF-3 and/or CHEF-2 and/or CHEF-1 of the invention.

In another aspect, the invention provides an expression vector capable of expressing both a CHEF of the invention, e.g. CHEF-3, CHEF-2 or CHEF-1, and another porcine cytokine, preferably one with which it synergistically interacts, particularly to enhance hematopoietic differentiation, and xenogeneic porcine bone marrow engraftment. Preferred examples include the combination of CHEF-3 or CHEF-1 with porcine leukemia inhibitory factor (LIF).

In another aspect of the invention, the efficiency of transduction of porcine cells, particularly bone marrow and hematopoietic cells, is significantly enhanced when transduction is effected in a medium containing the vector to be introduced as well as one or more of the porcine cytokines of the invention. In general, porcine bone marrow cells are cultured in the presence of 20 ng/ml CHEF-1 and 100 ng/ml CHEF-3, with or without additional cytokines. By analogy to transduction experiments performed with other species, an increase in cellular proliferation of up to 200 fold may be expected, with significantly elevated efficiency of stem cell transduction and replication prior to transfer to the recipient.

Another aspect of the invention provides transfected porcine cells or tissue modified to express elevated amounts of the cytokine(s) of the invention. For example, the bone marrow stromal cells can be transfected or transduced with vectors expressing CHEF-1, a protein unique to the swine but essential for survival and growth of porcine bone marrow. The modified stromal cells can then be co-transplanted with other porcine bone marrow cells and improve engraftment.

In another aspect, the porcine cytokines enhance the viability and maintenance in culture of totipotent or pluripotent stem cells, including primordial germ cells as well as inner cell mass-derived cells. These stem cells can be modified and selected in culture for expression of genes of interest, including but not limited to genes encoding transplantation antigens. Such stem cells, which require the porcine cytokines for growth in culture as undifferentiated cells, can differentiate into any somatic or germline cell type when reassociated with a developing host embryo at the preimplantation stage. Some animals generated by that route from stem cells modified to express genes of interest will produce gametes carrying the modification and can be bred to generate lines appropriately expressing the modification. Alternatively, modified stem cells can be used to generate transgenic animals using the nuclear transfer procedure, where stem cell nuclei are introduced into a non-fertilized, enucleated oocyte and give rise to genetically uniform offspring carrying the modification. By analogy to the mouse system, we anticipate that in the pig at least some of the porcine cytokines (e.g. CHEF-3 and CHEF-3/LIF combinations) serve physiological functions which include germ cell development. As in the mouse, the porcine homolog of Stem Cell Factor, CHEF-3, is likely to be a critical component for culturing embryonic germ cells derived from genital ridges of early postimplantation embryos (days 23 to 30 post estrus). CHEF-3 can be provided for this purpose as a soluble factor in concentrations of 1 ng/ml to 1 ug/ml or as a membrane-bound constituent of feeder cells. The end result is the capacity to produce transgenic strains of swine that express a novel phenotype, such as a trait or protein product, i.e., a modified immunological profile of a particular organ intended for xenogeneic transplant donation that renders it immunologically more similar to the homologous recipient organ's immunological profile.

The porcine cytokines of the invention are also useful as "lead compounds" that can be modified or whose structure/function interactions with receptors or other molecules can be studied to synthesize or screen for low molecular weight mimetics or antagonists. Such modifications could include those designed to increase the activity of the compound on its target cells, increase the pharmacological half-life, provide enhanced species specificity, or reduce the antigenicity of the compound.

Another principal aspect of this invention is a method of inducing tolerance in a xenogeneic transplantation host, such as a human recipient, of a porcine organ by introducing the porcine CHEF cytokines, combinations of them or combinations of them with other porcine cytokines per se or in combination with porcine bone marrow or hematopoietic cells, whether fully differentiated or as expanded cultures of progenitor cells, to the intended recipient prior to introduction of the porcine transplant organ.

In the case of xenogeneic transplantation of tissue or organs, the donor of the implant and the animal that supplies the tolerance-inducing bone marrow is preferably of the same immunological profile. For example, it is preferable to derive implant tissue from a colony of donors that is highly inbred. Implanted tissue may consist of organs such as liver, kidney, heart; body parts such as bone or skeletal matrix; tissue such as skin, intestines, endocrine glands; or progenitor stem cells of various types. Primarily contemplated for such transplants are the solid, formed and more highly specialized organs such as the liver, kidney, heart or lung.

Another aspect of the invention provides for the stimulation of bone marrow proliferation in swine bone marrow donors by administering one or more of the porcine cytokines of the invention or compositions containing one or more of them to the marrow donor swine prior to recovery of bone marrow therefrom. For example, it may be preferable for engraftment and the induction of tolerance to have a bone marrow harvest enriched in a specific progenitor cell population which is an improved transplantation product. This product would enhance engraftment and the induction of tolerance. It is also contemplated that the harvested bone marrow can be cultured ex vivo in the presence of various CHEFs to generate a bone marrow population which is an improved transplantation product. This product would enhance engraftment and the induction of tolerance.

Another aspect of the invention relates to a method of enhancing the proliferation of porcine bone marrow cells in a xenogeneic recipient which comprises exposing said cells to the porcine cytokine of the invention. A related aspect provides a method for enhancing engraftment of porcine bone marrow cells, in a recipient mammal by, prior to or simultaneous with transplantation of the tissue, introducing the porcine cytokine or mixtures thereof with other substantially pure porcine cytokines in accordance with the invention into the recipient. Modes of introducing and related information regarding dose ranges and administration routes, regimens, vehicles and the like are discussed below. The cytokine(s) can preferably be administered systemically by intravenous infusion.

Bone marrow cells (BMC) of the donor injected into the recipient home to appropriate sites of the recipient and grow contiguously with remaining host cells and proliferate, forming a chimeric lymphohematopoietic population. By this process, newly forming B cells (and the antibodies they produce) are exposed to donor antigens, so that the transplant will be recognized as self. Tolerance to the donor is also observed at the T cell level in animals in which BMC engraftment has been achieved. When an organ graft is placed in such a recipient after bone marrow chimerism has been induced, the graft is accepted by both the humoral and cellular arms of the immune system. The use of a porcine cytokine in accordance with the present invention preferentially stimulates the porcine bone marrow cells to provide engraftment thereof in the recipient.

The method of introducing bone marrow cells may be altered, particularly by (1) increasing the time interval between injecting BMC and implanting the tissue; (2) increasing or decreasing the amount of BMC injected; (3) varying the number of BMC injections; (4) varying the method of delivery of BMC; or (5) varying the source of BMC. Although BMC derived from the tissue donor is preferable, BMC may be obtained from other individuals or species, or from genetically-engineered inbred donor strains, or from in vitro cell culture.

In another aspect of the invention, it has been recognized that the novel porcine cytokines have additional utility in the prevention or treatment of various infections or diseases to which swine population are susceptible. Examples of such maladies include those for which the pig is especially reliant on granulocyte activity for recovery (e.g. African Swine Fever) or those which can lead to generalized immunosuppression (e.g. Hog cholera, Pseudorabies, Swine Influenza).

In another principal aspect of the invention, the CHEF proteins, fragments or other derivatives, or analogs thereof, or cells expressing them can be used as an immunogen to produce antibodies thereto. These antibodies can be, for example, polyclonal, monoclonal, chimeric, single chain, Fab fragments, or an Fab expression library. Various procedures known in the art may be used for the production of polyclonal antibodies. For preparation of monoclonal antibodies, any technique which provides antibodies produced by continuous cell line cultures can be used. Examples include the hybridoma technique (Kohler and Milstein, 1975, Nature 256:495–497), the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). Techniques described for the production of single chain antibodies (U.S. Pat. No. 4,946,778) can be adapted to produce CHEF-specific single chain antibodies. The antibodies can be used in methods relating to the localization and activity of the protein sequences of the invention, e.g., for imaging these proteins, measuring levels thereof in appropriate physiological samples and the like.

The present invention also provides pharmaceutical compositions. Such compositions comprise a therapeutically effective amount of the porcine cytokine, and a pharmaceutically acceptable carrier or excipient. Such a carrier includes but is not limited to saline, buffered saline, dextrose, water, glycerol, ethanol, and combinations thereof. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Modes of administration of the porcine cytokine include but are not limited to intravenous, intramuscular and subcutaneous routes. The compounds may be administered by any convenient route, for example by infusion or bolus injection and may be administered together with other biologically active agents. Administration is preferably systemic, e.g., by intravenous infusion separately or in combination (preferably admixture) with porcine bone marrow cells.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

The porcine cytokine(s) is used in an amount effective to promote engraftment of porcine bone marrow in the recipient. In general, such amount is at least 5 μg/kg body weight and most generally need not be more than 500 μg/kg. Preferably, it is at least about 20 μg/kg and usually need not be more than about 100 μg/kg. The cytokine will be administered for a period of at least 7 days but generally not to exceed 30 days, with a typical therapeutic treatment period of 7 to 14 days. The cytokine will preferably be administered either intravenously or subcutaneously, one to three times per day, and will be adjusted to meet optimal efficacy and pharmacological dosing.

The following examples illustrate the invention in various of its aspects without being a limitation on its scope. The examples set forth below are listed as follows:

EX 1—SPECIES SPECIFIC HEMATOPOICITY OF PORCINE CYTOKINES
EX 2—ISOLATION AND SEQUENCING OF THE PORCINE CHEF-3 cDNA GENE
EX 3—GST-CHEF-3 FUSION PROTEIN EXPRESSED FROM *E. COLI*
EX 4—EXPRESSION OF CHEF-3 IN COS CELLS AND DETECTION USING A PORCINE BONE MARROW ASSAY
EX 5—ISOLATION AND SEQUENCING OF THE PORCINE CHEF-2 cDNA GENE
EX 6—THIOREDOXIN-CHEF-2 FUSION PROTEIN EXPRESSED FROM *E. COLI*
EX 7—EXPRESSION OF CHEF-2 IN COS CELLS AND DETECTION USING A PORCINE BONE MARROW ASSAY
EX 8—ISOLATION AND SEQUENCING OF THE PORCINE CHEF-1 cDNA GENE
EX 9—GST-CHEF-1 FUSION PROTEIN EXPRESSED FROM *E. COLI*
EX 10—EXPRESSION OF CHEF-1 IN COS CELLS AND DETECTION USING A PORCINE BONE MARROW ASSAY
EX 11—SYNERGISTIC COMBINATION OF CHEF-3 WITH PORCINE LIF

EXAMPLE 1

Species Specific Hematopoicity of Porcine Cytokines

Sources for Peripheral Blood: Human volunteers were informed of the intent of the study and signed an informed consent for blood donation. The procurement of peripheral blood from animal donors (pig and cynomolgus monkeys [*Macaca fascularis*]) was in accordance with approved protocols for the care and use of laboratory animals.

Isolation of Peripheral Blood Mononuclear Cells: Peripheral blood was obtained from donors by venapuncture into heparinized Vacutainer® tubes (Becton Dickinson, Rutherford, N.J.). Peripheral blood was diluted with an equal volume of phosphate buffered saline and layered over Histopaque (specific gravity 1.077 gm/1, Sigma, St. Louis, Mo.) and centrifuged at 2000 rpm for 15 minutes. Low density mononuclear cells (PBMNC) were isolated at the media-Histopaque interface and washed twice in Iscove's Modified Dulbecco's Media (IMDM, GIBCO BRL, Gaithersburg, Md.) containing 20% fetal bovine serum (FBS, GIBCO BRL, Gaithersburg, Md.), 1% L-Glutamine (GIBCO BRL Gaithersburg, Md.), 1% Penicillin-streptomycin (solution of each antibiotic at 10,000 units/ml, GIBCO BRL Gaithersburg, Md.) and $1 \times 10^{-4}$M 2-mercaptoethanol (Sigma, St. Louis, Mo.).

Preparation of Lymphocyte Conditioned Media (LCM): Isolated PBMNC were adjusted to a cell concentration of $1 \times 10^6$/ml in Iscove's Modified Dulbecco's Media (IMDM, GIBCO BRL, Gaithersburg, Md.) containing 20% fetal bovine serum (FBS, GIBCO BRL, Gaithersburg, Md.), 1% 1-Glutamine (GIBCO BRL Gaithersburg, Md.), 1% Penicillin-streptomycin (solution of each antibiotic at 10,000 units/ml, GIBCO BRL Gaithersburg, Md.) and $1 \times 10^{-4}$M 2-mercaptoethanol. Phytohemaglutinin (PHA) (GIBCO BRL, Gaithersburg, Md.) was added to the cells at a concentration of 1 ml/100 ml media containing PBMNC. PBMNC, 100 ml, were placed into tissue culture flasks (162 cm$^2$, Costar, Cambridge, Mass.) and incubated for 7 days at 37° C., in a 5% $CO_2$ atmosphere. At the end of 7 days, the supernatant was harvested after pelleting the cells by centrifugation (2000 rpm, 10 minutes) and sterile filtered through a 0.22 mm filter (Costar, Cambridge, Mass.).

Bone Marrow Cells: Bone marrow was obtained from either pig or monkey bones. Monkey femurs were purchased from the Texas Primate Center (Hazelton Research Products, Alice, Tex.). Bones were harvested from the donor, shipped on wet ice overnight and bone marrow cells were isolated the following day. Pig bone marrow cells were isolated from ribs of pig kidney donors (Transplantation Biology Research Center, Massachusetts General Hospital, Charlestown, Mass.) on the same day as procurement. Under sterile conditions, bones are cut into smaller pieces and marrow is scraped and washed from the bone using a solution of Dulbecco's phosphate buffered saline (GIBCO BRL, Gaithersburg, Md.) containing 10% citrate phosphate dextrose solution (Sigma, St. Louis, Mo.) and gentamycin 100 mg/ml (GIBCO-BRL, Gaithersburg, Md.). Bone marrow cells (BMC) were washed several times with the phosphate buffered saline solution (used above) and resuspended in RPMI-1640 media (GIBCO BRL, Gaithersburg, Md.) containing 10% FBS and gentamycin at a cell concentration of $2 \times 10^6$ml in tissue culture flasks (15 ml per 75 cm$^2$ flask). BMC were incubated overnight at 37° C., 5% $CO_2$ after which time nonadherent cells were harvested from the flasks and washed with RPMI-1640 media. These cells were used in the clonogenic assay.

Clonogenic Assay: A titration of monkey BMC versus pig BMC was maintained where a combined total of pig and monkey BMC were plated at a concentration of 48–50,000 cells per ml of assay media. Four combinations were used in this study: $50 \times 10^3$ monkey:: $0 \times 10^3$ pig; $32 \times 10^3$ monkey:: $16 \times 10^3$ pig; $16 \times 10^3$ monkey:: $32 \times 10^3$ pig; and $0 \times 10^3$ monkey:: 50×10³ pig. In addition, to validate linearity of colony formation, monkey and pig BMC were plated separately at concentrations of 16 and 32×10³ ml. Media used in these assays was an IMDM based media with 30% FBS, either 5% pig LCM or 5% monkey LCM or both LCM at 5%, and 1.15% methylcellulose (Terry Fox Laboratories, Vancouver, BC). Control cultures did not contain any source of LCM. Cultures were plated in duplicate at 1 ml volumes in 35 mm plates (Nunc, Naperville, Ill.). Cultures were incubated for 7 days at 37° C., 5% $CO_2$ and colonies (composed of 50 cells or greater) were counted as a colony.

Proliferation Assay: A proliferation assay was used to compare the response of pig BMC to cytokines from different species. Pig BMC (2.5×104) were plated in each well of a 96 well "u" bottom tissue culture plate containing 200 ml of media. The media base was serum free, AIM-V media (GIBCO BRL, Gaithersburg, Md.) to this was added 0, 1, 3, 5, 7, or 10% LCM from either pig, monkey or human. Triplicate evaluations were performed for each LCM concentration. Cultures were incubated for 6 days at 37° C., 5% $CO_2$; after which time, 1 $\mu$Ci of tritiated thymidine [$^3$H-Tdr, (Amersham Corp., Arlington Heights, Ill.) was added and cultures were incubated for an additional 16 hours. Culture plates were harvested onto a glass fiber filter on the seventh day using a TOMTEC harvester (Tomtec Inc., Orange, Conn.). Radioactive samples were determined using a Betaplate reader (Wallac Inc., Gaithersburg, Md.) and results expressed as counts per minute.

The results of porcine specific molecules providing specific growth advantage to pig bone marrow cells in a mixture of monkey and pig bone marrow is illustrated in FIG. 1. In this culture system, pig cells responded only to the pig specific conditioned media and not to the monkey conditioned media. Monkey cells did respond to pig conditioned media but only 10% of what was observed in the presence of monkey conditioned media. Therefore, the preferential growth of the pig cells was accomplished by using pig specific factors.

Dose dependence and exceptional species specificity of porcine bone marrow cell proliferation was also demonstrated as shown in FIG. 2. Tritiated thymidine (T*) uptake by porcine bone marrow cells was measured when exposed to porcine, monkey and human LCM over a range of concentrations (V/V) of LCM in IMDM medium (%CM).

EXAMPLE 2

Isolation and Sequencing of the Porcine CHEF-3 cDNA Gene

Endothelial Cell Isolation and Culture: Endothelial cells were derived from miniature swine aorta by scraping the luminal surface of the blood vessel as described by Ryan et al. (Tissue and Cell, 12:619–635 1980). The cells were resuspended in M199 medium supplemented with 20% fetal bovine serum (GIBCO BRL, Gaithersburg, Md.) and gentamycin and plated in 25 cm² tissue culture flasks pre-coated with fibronectin (5 $\mu$g/cm²) and laminin (1 $\mu$g/cm²). Endothelial cell growth supplement (Collaborative Research, Bedford, Mass.) at 150 $\mu$g/ml was added only at the beginning of the culture. The cultures were maintained by changing one half of the media every 2–3 days. The subculture was passaged by treating the cells with 0.25% trypsin-EDTA (Gibco BRL) for 2 minutes when the monolayer was confluent. Cultures consisted of homogeneous cells with typical endothelial cell morphology. The cells were subcultured four times before they were used for messenger RNA isolation.

Oligonucleotides: The following oligonucleotides were purchased from Oligos Etc., (Wilsonville, Oreg.):

1. dL-1 (SEQ ID NO 1): 5'-GCGCTGCCTT TCCTTAT-GAA G. dL-1 is a 5' end primer including 15 nucleotides of 5' untranslated region and the first two codons of the signal peptide for human Stem Cell Factor (Martin, F. H. et. al. Cell, 63:203–211 (1990)).

2. FC-1 (SEQ ID NO 2): 5'-TTAGGCTTTC CTAT-TACTGC TACT. FC-1 is a 3' end primer (reverse complement of transcribed sequence) with the first three nucleotides comprising an artificial stop codon and the remaining 21 nucleotides complementary to the sequence encoding amino acids 173–179 of secreted form of murine Stem Cell Factor (Anderson, D. H. et. al. Cell, 63:235–243 (1990)).

RNA Isolation and RNA PCR: RNA was extracted from pig aortic endothelial cells by lysis in 4M guanidine isothiocyanate and ultracentrifugation through 5.7M cesium chloride. Total RNA (1 $\mu$g) was reverse transcribed using the RNA PCR kit purchased from Perkin-Elmer Cetus (Norwalk, Conn.). Annealing and reverse transcriptase extension conditions were 25° C. for 5 minutes, 37° C. for 5 minutes, 42° C. for 25 minutes. Subsequent amplification was performed with the addition of the dL-1 5' oligonucleotide primer and cycle conditions of 94° C. for 1 minute, 50° C. for 1 minute, 72° C. for 1 minute with a final extension at 72° C. for 7 minutes. The fragment was gel purified on 1% agarose and subcloned directly into the Eco RV site of pBluescript KS II+(Stratagene, La Jolla, Calif.) to create pCHEF-3.

The sequence of the CHEF-3 cDNA gene was determined by sequencing multiple subclones of the dL-1/Fc-1 PCR product by the dideoxy chain termination method using the Sequenase™ T7 polymerase kit (US Biochemical, Cleveland, Ohio). All sequences were in agreement with that determined for the insert portion of pCHEF-3.

DNA and protein sequence comparisons were made using the GeneWorks sequence analysis package (Intelligenetics, Mountain View, Calif.) and sequences from the following sources:

1) Human Stem Cell Factor: Martin, F. H. et. al. Cell, 63:203–211 (1990). GenBank accession number M59964.

2) Murine Stem Cell Factor: Anderson, D. H. et. al. Cell, 63:235–243 (1990). GenBank accession number M38436.

3) Rat Stem Cell Factor: Martin, F. H. et. al. Cell, 63:203–211 (1990). GenBank accession number M59966.

FIG. 3 shows the nucleotide (SEQ ID NO: 3) and predicted amino acid (SEQ ID NO: 4) sequences of the CHEF-3 coding region. The insert of pCHEF-3 is comprised of the sequence of dL-1 (nucleotides 1–21) joined to authentic porcine sequence (nucleotides 22–609) joined to the reverse complement of FC-1 sequence (nucleotides 610–633). Protein expression in mammalian cells should initiate with the methionine encoded by nucleotides 1–3 and terminate with an alanine encoded by nucleotides 613–615. Based on studies with stem cell factor from other species, mammalian cells are predicted to secrete a protein beginning with a glutamine encoded by nucleotides 76–78 (bold) derived from the above by signal peptide cleavage. In comparable regions, the CHEF-3 cDNA gene has nucleic acid homologies of 91%, 87%, and 86% with Stem Cell Factor from human, mouse, and rat species respectively. All are single nucleotide substitution except for an insertion of 3 nucleotides in the pig CHEF-3 gene. At the amino acid level, CHEF-3 is 83% similar to rat and human Stem Cell Factor , while CHEF-3 and mouse Stem Cell Factor are 80% similar.

EXAMPLE 3

GST-CHEF3 Fusion Protein Expressed from *E. coli*

This example describes a method for construction of the vector pMDR1069 (a glutathione-S-transferase gene fusion protein expression vector).

pCHEF-3 was modified in order to insert an EcoRI site following the translation termination codon at the 3' end of the CHEF-3 sequence. pCHEF-3 was cleaved with HindIII, the terminii were "filled-in" using the Klenow fragment of DNA polymerase I (Boehringer Mannheim Biochemicals, Indianapolis, Ind.). EcoRI linkers (pCGGAATTCCG [SEQ ID NO: 5] New England BioLabs, Inc., Beverly, Mass.) were ligated to the HindIII cleaved pCHEF-3. Prior to transformation of *E. coli* JM101 HindIII was added to the ligation reaction in order to linearize any recircularized pCHEF-3. Ampicillin resistant colonies were screened for the presence of a 650 bp EcoRI fragment. The resulting vector is described as pMDR1068. pMDR1068 was cleaved using PstI and EcoRI and the approximately 650 bp fragment was isolated by LMA (low melting-temperature agarose).

pGEX-2T was purchased from Pharmacia LKB Biotechnology, Piscataway, N.J. 08854. The plasmid-pGEX-2T is designed for inducible high-level expression of genes as a fusion with Schistosoma japonicum glutathione-S-transferase (GST). Cleavage of the 26 kDa GST domain from the fusion protein is facilitated by the presence of a recognition sequence for thrombin immediately upstream from the mulitple cloning site. pGEX-2T was cleaved with EcoRI, dephosphorylated and cleaved with BamHI. The 4.9 Kb fragment was isolated by LMA.

Oligonucleotides CHE02 and CHE03 were synthesized using an Applied Biosystems Inc. (Foster City, Calif.) oligonucleotide synthesizer.

CHE02 (SEQ ID NO: 6): 5'-GATCACAAGG GATCT-GCA

CHE03 (SEQ ID NO: 7): 5'-GATCCCTTGT

The DNA fragments and oligonucleotides were ligated and the ligation mix was used to transform *E. coli* JM101. Ampicillin resistant colonies were screened for the presence of a 1500 bp PstI fragment. The resulting plasmid is described as pMDR1069

Expression of the GST-CHEF-3 Fusion Protein from pMDR1069: A single colony of pMDR1069 in *E. coli* JM101 was grown overnight in Terrific Broth (TB). Sambrook, et al., Molecular Cloning: A Laboratory Manual, Cold Spring Harbor Press) containing 50 μg/ml Ampicillin. 0.5 ml of the overnight culture was added to 50 ml TB+50 μg/ml Ampicillin) and grown at 37° C. with vigorous shaking (350 r.p.m.) until the culture reached an optical density of 1 measured at 600 nm. An aliquot was removed as the pre-induction sample and then isopropyl-b-D-thiogalactopyranoside (IPTG) was added to a final concentration of 1 mM. Aliquots were removed at 1, 3, 5 and 16 hrs post-induction. The cells were centrifuged, resuspended in reducing buffer for protein gels and boiled for 10 min prior to analysis by 10% polyacrylamide-SDS gel electrophoresis. The gel was stained using Coomassie Blue. Cells containing the plasmid pGEX-2T were analysed as the negative control. The presence of a protein band at approximately 46 kDa indicates the induction of the GST-CHEF-3 fusion protein.

FIG. 4 shows an SDS-PAGE analysis of lysates prepared as above. Samples prior to induction with IPTG (PRE) and following a 5 hour induction with IPTG (POST) were analyzed with protein molecule weight markers indicated (in kDa). The induced GST-CHEF-3 fusion protein is indicated by the arrow.

EXAMPLE 4

Expression of CHEF-3 in COS cells and detection using a porcine bone marrow assay Construction of pCHEF-3EXP.pcd, a eukaryotic expression vector for a secreted form of CHEF-3 protein: pCHEF-3 was cleaved within the polycloning site flanking the CHEF-3 insert with EcoRI and XhoI and the 560 bp fragment was isolated from low melting temperature agarose (LMA). pcDNAI/Amp was purchased from Invitrogen Corporation (San Diego, Calif.). pcDNAI/Amp facilitates high level transient expression of recombinant proteins in eukaryotic cells. The plasmid was cleaved with EcoRI and XhoI and dephosphorylated using calf alkaline phosphatase. The vector fragment was purified from LMA. The DNA fragments were ligated and the ligation mix was used to transform *E. coli* JM101. Ampicillin resistant colonies were screened for the presence of 570 bp fragment. The resulting plasmid, pCHEF-3EXP.pcd, contains the entire sequence of pCHEF-3 (SEQ ID NO:3) insert shown in FIG. 3.

Expression of CHEF-3 from transiently transfected COS cells: COS7 cells were obtained from the ATCC (Rockville, Md.) and are grown in DMEM+10% fetal calf serum (DMEM-10). The COS7 cells were transfected using 2 μg/ml DNA and 15 μg/ml LIPOFECTIN Reagent (Gibco BRL) in Opti-MEM serum-free medium (Gibco BRL) for 5 hrs, after which time the medium was replaced with DMEM-10. Cells were allowed to grow for 72 hrs and the supernatant medium was collected, filtered and assayed for the presence of CHEF-3.

Detection of CHEF-3 in Transfected COS Cell Supernatant: Pig BMC were plated in 96 well "U" bottom tissue culture plates at a concentration of $2.8 \times 10^4$ cells per well. The media base was Modified Eagles media (MEM-199, GIBCO BRL, Gaithersburg, Md.) containing 13% FBS; this media was made 5% (V/V) with concentrated (12-fold) supernatants from either mock-transfected COS cells or either pCHEF-3EXP.pcd transfected COS cells. Cultures were incubated for 5 days at 37° C., 5% $CO_2$; each well was pulsed with one microcurie $^3$H-Tdr and incubated for an additional 16 hours. Culture plates were harvested onto a glass fiber filter using a TOMTEC harvester (Tomtec Inc., Orange, Conn.). Radioactive content of the samples was determined using a Betaplate reader (Wallac Inc., Gaithersburg, Md.) and results expressed as counts per minute.

Figure 5:
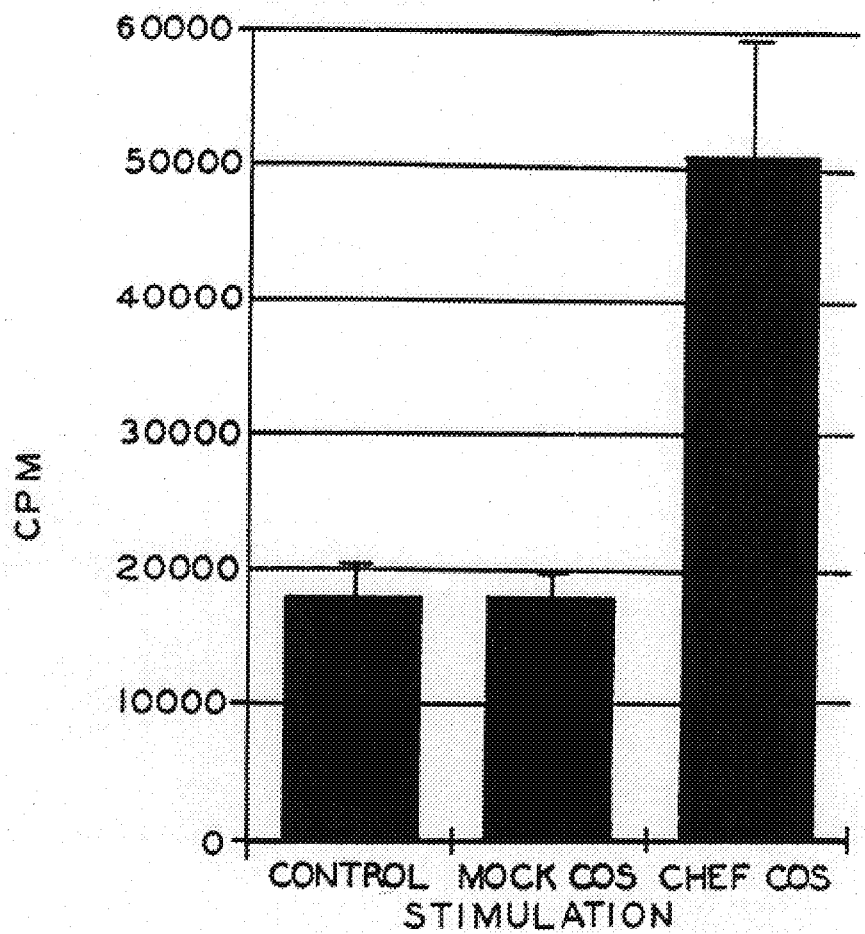
FIG. 5 shows the proliferative response of pig BMC to the stimulus provided by supernatant from COS cells transfected with the pCHEF-3 construct, as described in Example 4. The material from the mock transfected cells did not stimulate proliferation.

FIG. 5 shows the proliferative response of pig bone marrow cells in the presense of no additional agent (control), COS supernatants from cells transfected with pcDNAI/Amp (mock COS) or COS supernatant from cells transfected with pCHEF-3EXP.pcd (CHEF COS) assayed as described above.

EXAMPLE 5

Isolation and Sequencing of the Porcine CHEF-2 cDNA Gene

RNA isolation from peripheral blood lymphocytes: Peripheral blood mononuclear cells from human volunteers and miniswine were isolated as described in Example 1. Total RNA was isolated according to the method of Chergwin (Biochemistry, 18:5294, 1979). Poly A+ RNA was isolated using poly-U Sephadex chromatography (GIBCO BRL, Gaithersburg, Md.) according to the manufacturer's instructions.

Human GM-CSF cDNA isolation: Total RNA from human peripheral blood mononuclear cells (PBMCs) cultured in the presence of 1% phytohemaglutinin (PHA; GIBCO BRL). for 72 hours (1 μg) was reverse transcribed and used in a polymerase chain reaction (PCR) as described in Example 2. The following primers were used:

1) Reverse transcription primer: XN-2 (SEQ ID NO: 14) 5'-TGGTTCCCAG CAGTCAAAGG G. XN-2 is the reverse complement of nucleotides 416–436 of the ovine GM-CSF cDNA gene (McInnes, C. J. and Haig, D. M. Gene 105:275–279 (1991). GenBank accession number Z18291).

2) Forward PCR primer: XW3 (SEQ ID NO: 8), 5'-TTGGGCACTG TGGCCTGCAG C. XW3 is derived from nucleotides 57–77 of the human GM-CSF cDNA gene (Lee, F. et. al. Proc. Natl. Acad. Sci. U.S.A. 82:4360–4368 (1985). GenBank accession number M14743.).

3) Reverse PCR primer: XW4 (SEQ ID NO: 9), 5'-ACAGGAAGTT TCCGGGGTTG G. XW4 is the reverse complement of nucleotides 351–371 of the human GM-CSF cDNA gene (Lee, F. et. al. Proc. Natl. Acad. Sci. U.S.A. 82:4360–4368 (1985). GenBank accession number M14743.).

The resulting 315 bp fragment was subcloned into the EcoRV site of pBluescript KS+ (Stratagene, LaJolla, Calif.) using standard methods, generating plasmid phuGM#23. Randomly primed probes (T7 Quickprime; Pharmacia, Piscataway, N.J.) were prepared using the cloned insert isolated from a low melting temperature agarose gel T7 RNA polymerase antisense transcripts were made using the Riboprobe transcription kit (Promega, Madison, Wis.).

Porcine lymphocyte conditioned media and lymphocyte RNA analysis: Porcine (miniswine) PBMC were cultured essentially as described in Example 1. Cells were treated with either 1% phytohemaglutinin (PHA), PHA and 5ng/ml phorbol 12-myristate 13-acetate (PHA+PMA; Sigma, St. Louis, Mo.), or no additional agents (Control) for 24 hours. On day 1 (immediately following treatment) cells were washed and split into 4 aliquots of fresh media without additional treatment. RNA was isolated from 1 aliquot of cells, and the corresponding conditioned media collected, on days 2–5.

Filtered supernatants were assayed for the presence of proliferation stimulating activity as follows. Pig bone marrow cells, at 25,000 cells per well, were placed in a 96 well tissue culture plate. Each well contained 200 μl of media (Iscove's Modified Dulbecco's Media, 10% fetal bovine serum, and 10% (v/v) conditioned media). Cultures were plated in triplicate and incubated at 37° C. for 7 days. On day 6, each well was pulsed with 20 μl of media containing $^3$H-Tdr (1 microcurie per well). Cells were harvested using a Harvester (Tomtec) and incorporated $^3$H-Tdr was detected using a Beta plate reader. Values are means of the triplicate wells.

RNA was fractionated on agarose-formaldehyde gels as described (T. Maniatis, ed., Molecular Cloning: A Laboratory Manual) and transferred to nylon membranes (GeneScreen; DuPont NEN) according to the manufacturer's instructions. The RNA blot was hybridized with 5×10$^5$ cpm/ml human GM-CSF antisense RNA probe in 5×SSPE (1×SSPE is 0.15M NaCl, 0.01M NaH$_2$PO$_4$, 0.001M EDTA), 50% formamide buffer at 42° C. and washed in 2×SSPE, 0.1% sodium dodecyl sulfate at 62° C.

cDNA library construction and screening: Poly A+ RNA was isolated from porcine peripheral blood mononuclear cells 5 days after a 16 hour treatment with PHA as described above. Double-stranded cDNA (dscDNA) with Eco RI adapters was prepared using the Timesaver cDNA synthesis kit (Pharmacia) according to the manufacturer's instructions. The dscDNA was ligated into the lambda replacement vector λgt-10 (Stratagene, LaJolla, Calif.) and packaged using the Packagene kit (Promega). The resulting phage were amplified on E. coli strain NM514. For screening, 1×10$^5$ amplified phage were plated on 150 mm plates using strain C600 Hfl. (Promega). Six (6) duplicate filter sets, containing phage amplified from 3×10$^5$ independent clones, were hybridized to randomly primed phuGM#23 plasmid insert in 5×SSPE buffer at 50° C. and washed in 2×SSPE buffer at 50° C. Putative positives from the first screen were subjected to a second round of screening as above. DNA from clone λNC1-1A, selected from the above, was prepared from liquid lysate culture for sequencing.

Sequencing of CHEF-2 cDNA clones: DNA from clone λNC1-1A was; sequenced from either end of the insert using λgt-10 forward and reverse sequencing primers and the fmol Sequencing Kit (Promega). After confirming substantial homology to GM-CSF sequences from other species, the insert was removed from lNC1-1A with Not I and subcloned into the Not I site of plasmid pcDNA I Amp (InVitrogen, San Diego, Calif.). One subclone, having the proper 5'–3' orientation relative to the vector CMV promoter, was designated pCHEF-2.pcd. The insert from pCHEF-2.pcd was sequenced completely on both strands using the Sequenase sequencing kit (US Biochemical, Cleveland, Ohio) as described in Example 2.

DNA and protein sequence comparisons were made using the GeneWorks sequence analysis package (Intelligenetics, Mountain View, Calif.) and sequences from the following sources:

1) Human GM-CSF: Lee, F. et. al. Proc. Natl. Acad. Sci. U.S.A. 82:4360–4368 (1985). GenBank accession number M14743.

2) Murine GM-CSF: Miyatake, S. et. al. EMBO J. 4:2561–2568 (1985). GenBank accession number K01850.

3) Ovine GM-CSF: McInnes, C. J. and Haig, D. M. Gene 105:275–279 (1991). GenBank accession number Z18291.

4) Bovine GM-CSF: Maliszewski, C. R. et. al. Mol. Immunol. 25:843–850 (1988).

Figure 6:
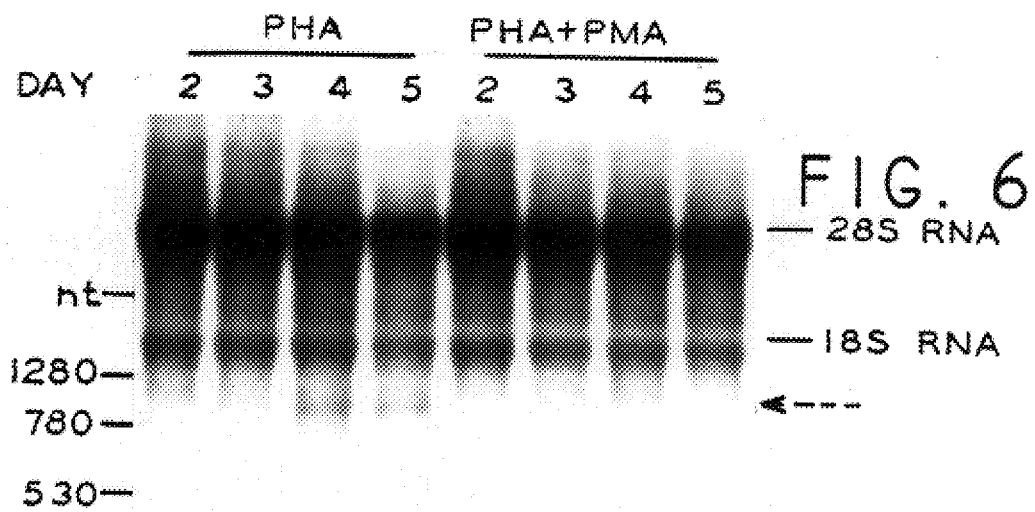
FIG. 6 shows a Northern blot of total RNA from porcine peripheral blood mononuclear cells hybridized under low stringency to an antisense RNA probe from human GM-CSF cDNA clone huGM#23 as described in Example 5.

As shown in FIG. 6, Northern blots of total RNA from porcine peripheral blood mononuclear cells were hybridized under low stringency to an antisense RNA probe from human GM-CSF cDNA clone phuGM#23. Cells were treated for 16 hours with PHA or PHA and PMA, washed, then harvested 2–5 days following initiation of treatment. A homologous transcript of approximately 800 nt (arrow) is induced by PHA treatment on days 4 and 5. A number of constitutively expressed transcripts cross hybridize to the probe under low stringency conditions.

Figure 7:
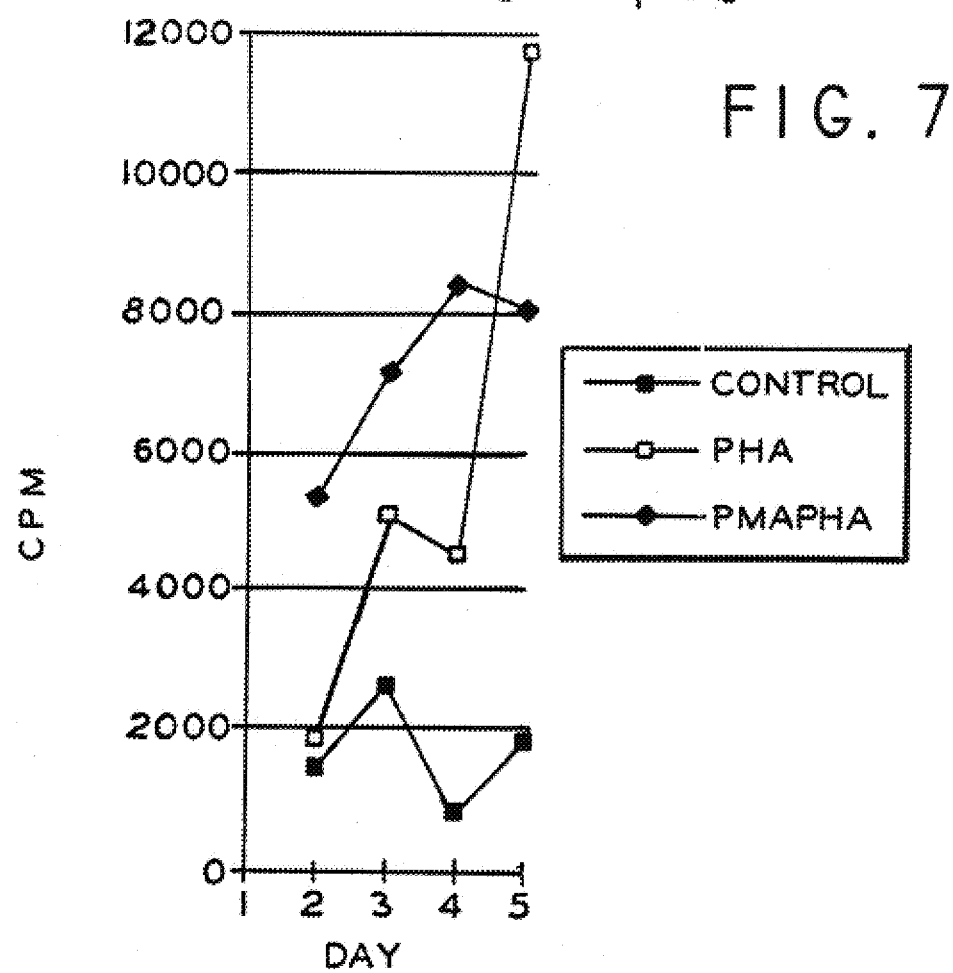
FIG. 7 shows the results of assay of conditioned media, harvested from cells used for RNA analysis as shown in FIG. 6, for porcine bone marrow proliferation activity, as further described in Example 5.

As shown in FIG. 7, conditioned media, harvested from cells used for RNA analysis as shown in FIG. 6, was assayed for porcine bone marrow proliferation activity. A significant increase in activity appears in media from PHA treated cells on day 5, following an induction of a transcript homologous to human GM-CSF on day 4.

FIG. 8 shows the nucleotide sequence (SEQ ID NO: 10) and derived amino acid sequence (SEQ ID NO: 11) of the CHEF-2 cDNA gene determined by sequencing clone llNC1-1A and subclone pCHEF-2.pcd. Expression in mammalian cells starts with the first ATG (position 23, bold), beginning a typical mammalian signal peptide, and continues to a TAA termination codon (position 455, bold). Nucleotides 1–7 (underlined) and 789–798 (underlined) are derived from the Not I/Eco RI adaptors used in construction of the cDNA library. Within the coding regions, CHEF-2 has nucleic acid homologies of 70%, 88%, 81% and 81% with GM-CSF from murine, ovine, human and bovine species respectively. Inclusive of the signal peptides, CHEF-2 has amino acid identities of 54% with murine, 80% with ovine, and 72% with human and bovine GM-CSF.

EXAMPLE 6

Thioredoxin-CHEF-2 Fusion Protein Expressed from E. coli

This example describes a method for construction of the vector pDA110 (a thioredoxin gene fusion protein expression vector).

Isolation of the mature CHEF-2 sequence: The 381 base pairs that code for the 127 amino acids corresponding to mature CHEF-2 (FIG. 8, nucleotides 81–461) were cloned using PCR technology. Two oligonucleotides were synthesized for amplification of the gene. Their sequences are shown below:

DA14 (sense primer; SEQ ID NO: 12):

5'-CGACGGTACC GGCTCCCACC CGCCCACCC

DA15 (antisense primer; SEQ ID NO: 13):

5'-AGGATCTAGA GGATCCTCAT CATTTTTGA

CTGGCCCCA

The oligonucleotides were designed such that the 5' end of the amplified fragment would contain a complete Kpn I site (GGTACC) and the 3' end a complete Xba I site (TCTAGA) downstream of the stop codon of the CHEF-2 gene. The Kpn I site was designed for the in-frame ligation of the CHEF-2 fragment to the 3' end of thioredoxin sequence.

Clone lNC1-1A contains the CHEF-2 cDNA. DNA isolated from this clone was amplified (Perkin Elmer DNA Thermal Cycler Model 480) in a 50 µl reaction containing 200 µM each dNTP, 0.5 µM each primer, 1.5 mM $MgCl_2$, 10 mM Tris (pH 8.3), 50 mM KCl, 8% dimethyl sulfoxide, and 0.25 units AmpliTaq DNA polymerase. The reaction was cycled for 0.5 min at 94° C., 1 min ramp to 55° C., 0.5 min at 55° C., 0.5 min ramp to 72° C., 0.5 min at 72° C., 1 min ramp to 94° C. for 35 cycles. The PCR products were analyzed on a 10% polyacrylamide gel. The major product band was about 400 bp, which is in good agreement with the expected size of 414 bp. Following the manufacturer's protocol, the DNA was purified using Magic PCR Preps (Promega, Madison, Wis.). The entire sample was digested first with Kpn I, then with Xba I. The Kpn I/Xba I fragment containing CHEF-2 was purified from the smaller fragments (<10 bp) by again, use of Magic PCR Preps.

Plasmid pTRXFUS (LaVallie et. al. Bio/Technology 11:187–193, 1993) was obtained from Genetics Institute (Cambridge, Mass.). pTRXFUS DNA was isolated using the Magic Maxi prep kit (Promega, Madison, Wis.) according to manufacturer's instructions. An aliquot of DNA (4 µg) was first digested with Kpn I, then digested with Xba I. Since only a <20 bp fragment is removed from the vector if both restriction enzymes successfully cut, the DNA was subsequently treated with alkaline phosphatase (calf intestinal).

The 3580 bp Kpn I/Xba I vector fragment was then purified on a 0.8% agarose gel. The vector fragment and the PCR fragment were ligated and transformed into competent E. coli strain GI698 (La Vallie et al., Bio/Technology 11: 187–193, 1993). Putative clones were screened by Hinc II restriction digest analysis. The resulting plasmid containing the gene encoding the thioredoxin-GM-CSF fusion protein is defined as plasmid, pDA110.

Expression of thioredoxin-CHEF-2: A single colony of E. coli GI698 (pDA110) was grown overnight at 23° C. in 2 mls modified M9CAA media, as described in La Vallie et al. containing 100 µg/ml ampicillin. The overnight culture was diluted (1:50) in 10 mls of fresh modified M9CAA containing 100 µg/ml ampicillin and was grown at 23° C. for two hours. One ml of culture was removed as the pre-induction sample and tryptophan (final concentration of 0.49 mM) was added to induce expression of thioredoxin-CHEF-2 After 18 hrs, one ml of culture was centrifuged. The pre- and post-induced cells were resuspended in SDS/reducing buffer and both were analyzed on a 12% SDS polyacrylamide gel. Plasmid pTRXFUS was used as a positive control for expression. The gel was stained with Coomassie blue and a new protein band at about 27.3 kDa was observed in the post-induced but not pre-induced sample. The size of this new protein band corresponds to the expected size of the thioredoxin-CHEF-2 fusion protein.

Figure 9:
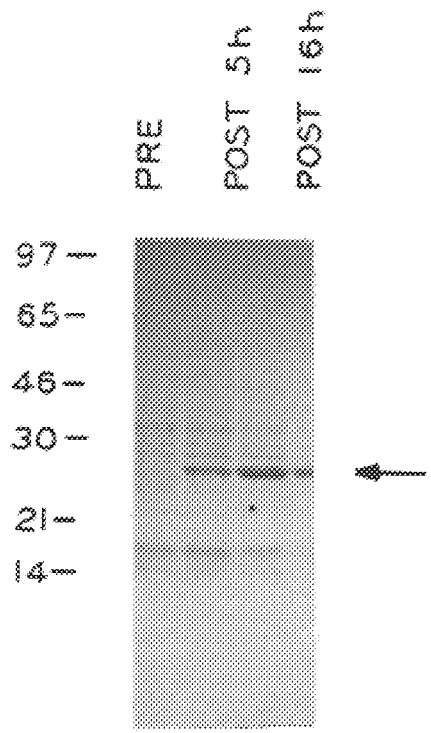
FIG. 9 shows an SDS-PAGE analysis of lysates of E. coli bearing plasmid pDA110, which encodes thioredoxin-CHEF-2 fusion protein, as described in Example 6. Samples prior to induction with IPTG (PRE) and following a 5 hour (POST 5 h) or 16 hour (POST 16 h) induction with IPTG (POST) were analyzed with protein molecule weight markers indicated (in kDa). The induced thioredoxin-CHEF-2 fusion protein is indicated by the arrow.

FIG. 9 shows an SDS-PAGE analysis of lysates prepared as above. Samples prior to induction with IPTG (PRE) and following a 5 hour (POST 5 h) or 16 hour (POST 16 h) induction with IPTG (POST) were analyzed with protein molecule weight markers indicated (in kDa). The induced thioredoxin-CHEF-2 fusion protein is indicated by the arrow.

EXAMPLE 7

Expression of CHEF-2 in COS Cells and Detection using a Porcine Bone Marrow Assay Construction of pCHEF-2EXP.pcd, a eukaryotic expression vector: pCHEF-2.pcd was digested at a unique Xcm I site within the CHEF-2 insert region (nucleotide 574 of FIG. 8) and at a unique Xho I site within the pcDNA I/Amp polylinker region downstream of the Not I insertion site. The protruding ends were blunted with Klenow fragment and the DNA recircularized with T4 DNA ligase. Clone pCHEF-2EXP.pcd was isolated from E. coli transformants of the above DNA and shown by DNA sequencing to differ from pCHEF-2.pcd by the deletion of CHEF-2 sequences 3' to nucleotide 574 of FIG. 8. As this region contains multiple repeats of the sequence ATTTA, previously associated with instability of eukaryotic mRNA molecules, the deletion should permit higher level accumulation of CHEF-2 RNA in COS cells. As nucleotide 480 is 3' to the translational stop codon of CHEF-2, there is no alteration of the expected amino acid sequence shown in FIG. 8.

Expression of CHEF-2 from transiently transfected COS cells: CHEF-2 was expressed by transient expression of COS cells as described for CHEF-3 in Example 4.

Detection of GM-CSF Proliferative Activity in COS Cell Supernatants: Pig bone marrow cells (BMC), obtained from pig donor 10758, were harvested aseptically from the femurs, washed in phosphate buffered saline solution, and decanted to remove bone particles. BMC were subsequently separated by continuous-flow centrifugal elutriation using a rotor speed of 2040 rpm and increasing flow rates of 50 and 70 ml/min to elute cells with increasing densities and size. Fractions collected at these flow rates were number 1 and 2.

After fraction 2 was collected, both the rotor and fluid flow was stopped, causing the cells remaining in the chamber to pellet. These were harvested from the chamber and represented fraction 3 cells which were used for the proliferation assay.

Fractionated pig bone marrow cells (25,000 cells per well) in Iscove's Modified Dulbecco's Media and 10% fetal bovine serum were added to 96 well microtiter plates to which increasing concentrations of COS cell supernatants were added adjusting the final volume to 200 µl/well. Cells were incubated at 37° C. for 3 days; on day 2, cells were pulsed with $^3$H-Tdr (1 microcurie per well). and wells were harvested 24 hours later. Counts were determined on a Beta Plate reader and expressed as a mean value of 3 wells.

Figure 10:
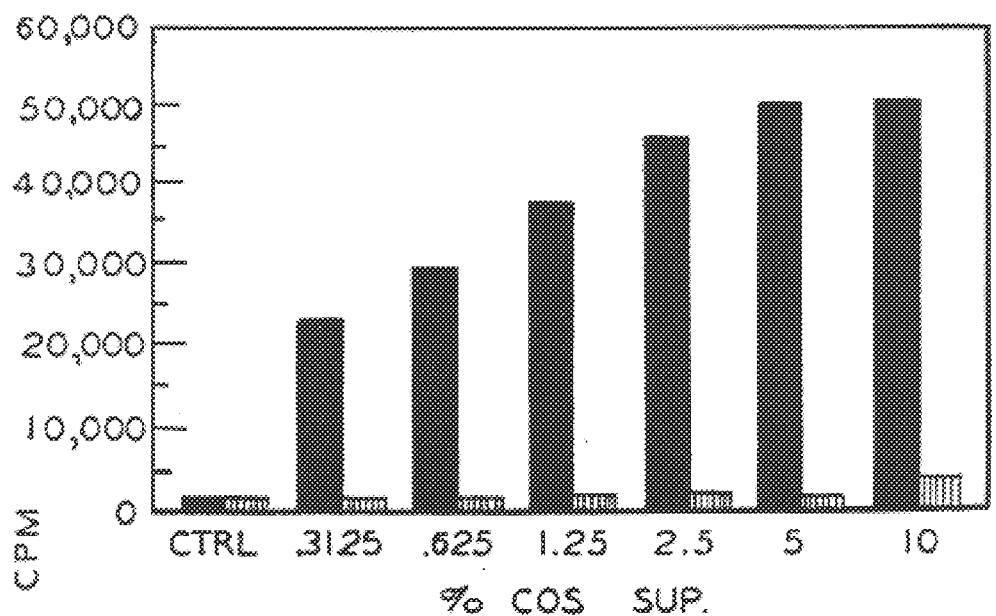
FIG. 10 shows the detection of GM-CSF proliferative activity in COS cell supernatants of COS cells transfected with a plasmid containing the CHEF-2 expression plasmid pCHEF-2EXP.pcd (pGM-CSF) or with pcDNA I/Amp alone (Mock-CM), as described in example 7.

FIG. 10 shows the detection of GM-CSF proliferative activity in COS cell supernatants of COS cells transfected with the CHEF-2 expression plasmid pCHEF-2EXP.pcd (pGM-CSF) or with pcDNA I/Amp alone (Mock-CM).

EXAMPLE 8

Isolation and Sequencing of the Porcine CHEF-1 cDNA Gene

Figures 11, 13:
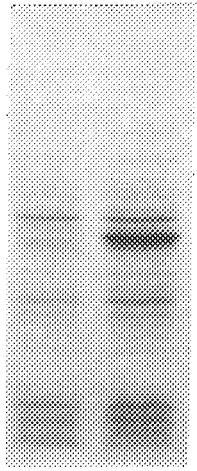
FIG. 11 diagrammatically illustrates the steps for the cloning of CHEF-1, described in Example 8. A restriction map of genomic DNA isolated is shown below in a scale in kilobases (S:Sfi I; X: Xba I; Z: Xho I). Line figures at the bottom represent phage isolated in the two screenings of the porcine genomic library. Regions encoding the porcine GM-CSF (CHEF-2) and porcine IL-3 (CHEF-1) genes are indicated.
FIG. 13 shows an SDS-PAGE analysis of lysates prepared from E. coli bearing plasmid pEXIL-4, which encodes GST-CHEF-1 fusion protein, as described in Example 9. Samples prior to induction with IPTG (PRE) and following a 3.5 hour (POST) induction with IPTG (POST) were analyzed with protein molecule weight markers indicated (in kDa). The induced GST-CHEF-1 fusion protein is indicated by the arrow.

Isolation of a genomic clone containing the porcine IL-3 (CHEF-1) gene: A genomic library was constructed in the vector λgem-12 (Promega, Madison, Wis.) using a Sau 3AI partial digest of miniswine (genotype a/a) peripheral blood mononuclear cell DNA. The library was screened with the cDNA insert of clone pCHEF-2.pcd (Example 5) to isolate 3 overlapping clones containing at least a portion of the porcine genomic sequence for GM-CSF (FIG. 11, clones λS1-2, λS4-1 and λS4-2). The orientation of the clones with respect to the direction of transcription of the CHEF-2 gene was determined by hybridizing Southern blots of phage restriction digests with oligonucleotide probes specific for exons 1 (XN1; (SEQ ID NO:24): 5'-AGGATGTGGC TGCAGAACCT G) or exon 4 (C2X4; (SEQ ID NO:15): ACATCTGCCA TTTCCCCTGC C) of the CHEF-2 gene. Sequences upstream of the CHEF-2 gene (a 1.7 kb Xba I fragment from phage λS4-2; coordinates 23–25 of FIG. 11) were used to rescreen the genomic library. Overlapping clones were isolated and restriction mapped. One clone, λS1E-3, was found to contain sequences from 6 through 22 kb upstream of the CHEF-2 promoter. This clone hybridized oligonucleotide probe OL-2 (SEQ ID NO: 16; 5'-CTATGGAGGT TCCATGTCAG ATAAAG) the sequence of which is conserved among the promoter regions of primate, ovine and rodent species. The clone also hybridized to oligonucleotide probe ILX5 (SEQ ID NO: 17; 5'-ATGTTCATTT GTACCTC) the sequence of which is conserved among the 3' untranslated regions of the same species. Genomic DNA sequence was obtained using the same two primers, and this sequence used to design oligonucleotides ILP-F (SEQ ID NO: 18; 5'-AGACAGGATC CATCGTACCG) and ILP-R (SEQ ID NO: 19; 5'-CTCATTCAGA AGGAGCAGGC) containing sequences from the presumptive 5' and 3' untranslated regions of the CHEF-1 gene, based upon the location of sequences homologous to OL-2 and ILX5 relative to the transcriptional start and polyadenylation sites of the IL-3 gene in other species.

Isolation of a cDNA encoding CHEF-1: Primers ILP-F and ILP-R were used to generate a PCR product of approximately 800 bp from oligo dT primed cDNA derived from poly A+ RNA from pig peripheral blood mononuclear cells 4 days after treatment with PHA, prepared as described in Example 5. This product was digested with Bam HI (which cuts within the ILP-F sequence) and cloned into the Bam HI/Eco RV site of pcDNA I/Amp. One clone was designated PCHEF-1.pcd1 and sequenced.

Sequencing of the CHEF-1 gene: Dideoxy sequencing was performed on PCR derived cDNA clone pCHEF-1.pcd1 and the exonic regions of C1G-2, an Eco RI subclone of λS1E-3 containing the CHEF-1 genomic gene (coordinates 29–35 of FIG. 11). Genomic sequence was obtained for all protein coding exon regions, and cDNA sequence was obtained along the entire length of the pCHEF-1.pcd1 insert. Together, this sequence comprised both strands of the CHEF-1 protein coding region in its entirety. Genomic and cDNA sequences were in complete agreement throughout the protein coding region.

DNA and protein sequence comparisons were made using the GeneWorks sequence analysis package (Intelligenetics, Mountain View, Calif.) and sequences from the following sources:

1) Human IL-3: Yang, Y.-C. et. al. Cell 47:3–10 (1986). GenBank accession number M14743.
2) Murine IL-3: Fung, M. C. et. al. Nature 307:233–237 (1984). GenBank accession number K01850.
3) Ovine IL-3: McInnes, C. J. et. al. Unpublished. GenBank accession number Z18291.
4) Gibbon IL-3: Yang, Y.-C. et. al. Cell 47:3–10 (1986). GenBank accession number M14744.

FIG. 11 diagramatically presents the CHEF-1 cloning steps. A restriction map of genomic DNA isolated is shown below a scale in kilobases (S: Sfi I; X: Xba I; Z: Xho I). Line figures at the bottom represent phage isolated in the two screenings of the porcine genomic library. Regions hybridizing to GM-CSF (CHEF-2) and IL-3 (CHEF-1) oligonucleotide probes are indicated.

FIG. 12 shows the nucleotide sequence (SEQ ID NO: 20) and derived amino acid sequence (SEQ ID NO: 21) of pCHEF-1.pcd1. The first ATG (bold) heads an open reading frame starting at nucleotide 24, beginning with a typical mammalian signal peptide, and continuing to a TAA termination codon beginning at nucleotide 456 (bold). Underlined sequences are derived from PCR primers ILP-F (nucleotides 1–15, underlined) and the reverse complement of ILP-R (nucleotides 740–760, underlined) used to isolate the CHEF-1 cDNA by PCR. Within the coding regions of the genes, CHEF-1 has nucleic acid homologies of 66%, 47%, 47% and 52% with the IL-3 genes of ovine, human, murine and gibbon species respectively. Inclusive of the signal peptides, CHEF-1 has amino acid identities of 46% with ovine, 34% with human, 26% with murine, and 33% with gibbon IL-3.

EXAMPLE 9

GST-CHEF-1 Fusion Protein Expressed from *E. coli*

This example describes a method for construction of the vector pEXIL-4 for the expression of soluble CHEF-1 in *E. coli*. Using the method of von Heijine (Nucleic Acids Research 14:4683–4690, 1986), the putative signal peptide cleavage site was determined to precede Met$_1$ of FIG. 12. The portion of the CHEF-1 cDNA gene encoding the mature (mammalian secreted form) is 363 nucleotides (FIG. 12, nucleotides 93–455) and encodes a 13.8 kDa protein.

Isolation of the mature CHEF-1 sequence by PCR: The following oligonucleotides were synthesized to amplify the 363 nucleotides of mature CHEF-1:

FE2Chf1: (SEQ ID NO: 22) 5' GGGGAATTCA TATGC-CTACC ACAACACTC. FE2Chf1 is a sense PCR primer that includes the first 18 nucleotides of mature CHEF-1 (underlined nucleotides). The $Met_1$ (ATG) codon is contained within an Nde I site (CATATG). In addition, upstream of the $Met_1$ is an Eco RI site (GAATTC).

REChf1: (SEQ ID NO:23) 5'CCAAGCTTG GATC-CTATTA GGGCTCTGTG ATCATGGG. REChf2 is an antisense PCR primer that includes tandem stop codons (TAA TGA) and the last 18 nucleotides of mature CHEF-1. Downstream of the stop codons are Bam HI (GGATCC) and Hind III: (AAGCTT) sites.

Primers FE2Chf1 and REChf1 were used to generate a PCR product of approximately 390 bp from pCHEF-1.pcd1 DNA, which contains the CHEF-1 cDNA cloned into the eukaryotic expression vector, pcDNAI/AMP. DNA was amplified (Perkin Elmer DNA Thermal Cycler Model 480) in a 50 µl reaction containing 200 µM each dNTP, 0.5 µM each primer, 1.5 mM $MgCl_2$, 10 mM Tris (pH 8.3), 50 mM KCl, 8% dimethyl sulfoxide, and 0.25 units AmpliTaq DNA polymerase. The reaction was cycled for 0.5 min at 94° C. , 1 min ramp to 55° C., 0.5 min at 55° C., 0.5 min ramp to 72° C., 0.5 min at 72° C., 1 min ramp to 94° C. for 35 cycles.

Construction of pEXIL-4 for expression of CHEF-1 in *E. coli*: The PCR products were analyzed on a 1% agarose gel. A major band was observed at the expected size of about 390 bp. The reaction mixture was phenol/chloroform extracted then ethanol precipitated. This fragment, and plasmid pGEX-KG (Guan and Dixon, Anal. Biochem. 192: 262–67, 1991), were both digested with Eco RI and Hind III then ligated. Competent *E. coli* JM109 cells were transformed with the ligation mixture. Positive clones were confirmed by restriction digest analysis with Eco RI/Hind III. The resulting plasmid containing GST-CHEF-1 is described as pEXIL-4.

Expression of GST-CHEF-1: A single colony of *E. coli* JM109 (pEXIL-4) was grown overnight at 37° C. in 2 mls Luria Broth (LB) containing 100 µg/ml ampicillin. The overnight culture was diluted (1:50) in 10 mls of fresh LB containing ampicillin and was grown at 37° C. for two hours. One ml of culture was removed as the pre-induction sample and IPTG was added to a final concentration of 1 mM. After 3.5 hrs, one ml of culture was centrifuged. The pre- and post induced cells were resuspended in SDS/reducing buffer and both were analyzed on a 12% SDS polyacrylamide gel. Plasmid pGEX-KG was used as a positive control for expression. The gel was stained with Coomassie blue and a new protein band at about 40 kDa was observed in the post-induced but not pre-induced sample. The size of this new protein band corresponds to the expected size of the GST-CHEF-1 fusion protein.

FIG. 13 shows an SDS-PAGE analysis of lysates prepared as above. Samples prior to induction with IPTG (PRE) and following a 3.5 hour (POST) induction with IPTG (POST) were analyzed with protein molecule weight markers indicated (in kDa). The induced GST-CHEF-1 fusion protein is indicated by the arrow.

EXAMPLE 10

Expression of CHEF-1 in COS Cells and Detection using a Porcine Bone Marrow Assay Construction of CHEF1EXP.pcd, a eukaryotic expression vector: pCHEF-1.pcd1 was digested to completion with Bam HI (nucleotide 2 of FIG. 12) and Hpa I (nucleotide 593 of FIG. 12) and the resulting 592 bp fragment recloned into the Bam HI/Eco RV site of pcDNA I/Amp. The resulting construct, pCHEF-1EXP.pcd, contained all coding sequences for CHEF-1, but was deleted of ATTTA instability sequences contained in the 3' untranslated region. Proper construction was verified by DNA sequencing.

Expression of CHEF-1 from transiently transfected COS cells: CHEF-1 was expressed by transient transfection of COS cells with pCHEF-1EXP.pcd, as described for CHEF-3 in Example 4.

Detection of CHEF-1 proliferative activity in COS cell supernatants: The detection of biological activity from COS cell supernatants transfected with pCHEF-1EXP.pcd or pcDNA I/Amp was assayed as follows. Pig bone marrow cells were plated at a concentration of 10,000 cells per well of a 96 well "U" bottomed culture plate in Iscove's Modified Dulbecco's Media containing 10% heat inactivated fetal bovine serum. The COS cell supernatants were added to this media at the appropriate percent (v/v). For three day assays, cultures were incubated for 2 days; 1 microcurie of $^3$H-Tdr was added; and plates were harvested on day 3. For seven day assays, cultures were incubated for 6 days; 1 microcurie of $^3$H-Tdr was added and plates were harvested on day 7. Results are counts per minute (cpm) and expressed as a mean value of triplicate wells.

Figure 14:
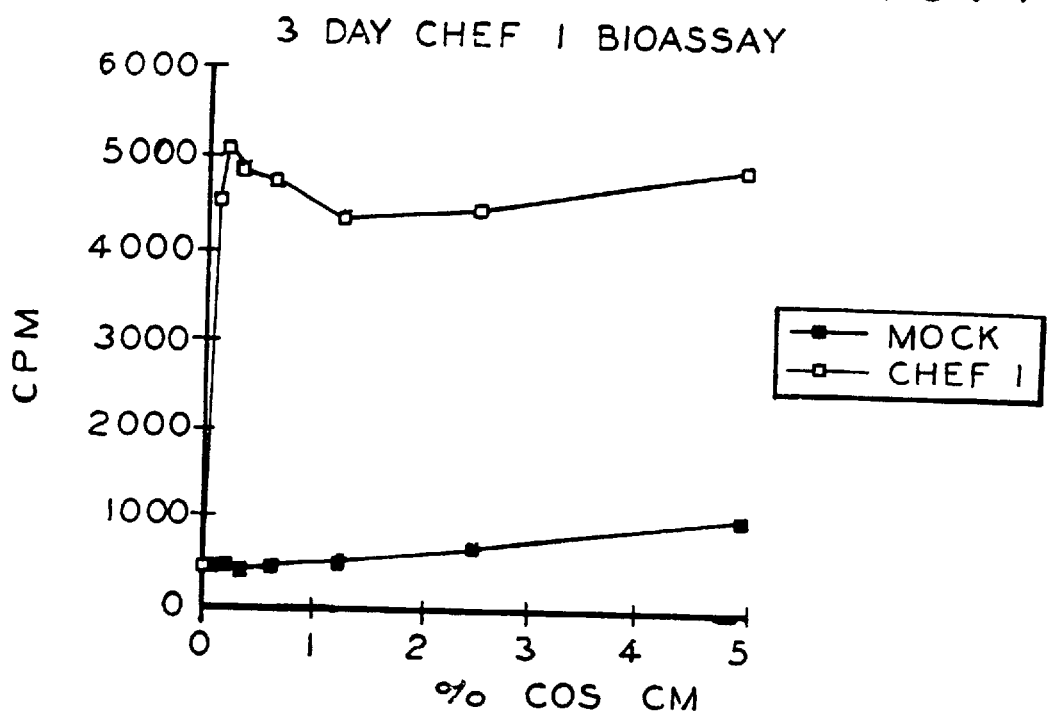
FIG. 14, illustrating results from Example 10, shows the proliferative response to COS cell supernatants containing CHEF-1 in a 3 day bioassay. An approximate 10-fold increase in cellular activity was detected with a dose of 0.078% conditioned medium, but with increasing doses of CHEF-1 further increases were not observed.

FIG. 14 shows the proliferative response to COS cell supernatants containing CHEF-1 in a 3 day bioassay. An approximate 10-fold increase in cellular activity was detected with a dose of 0.078% conditioned medium, but with increasing doses of CHEF-1 further increases were not observed.

Figure 15:
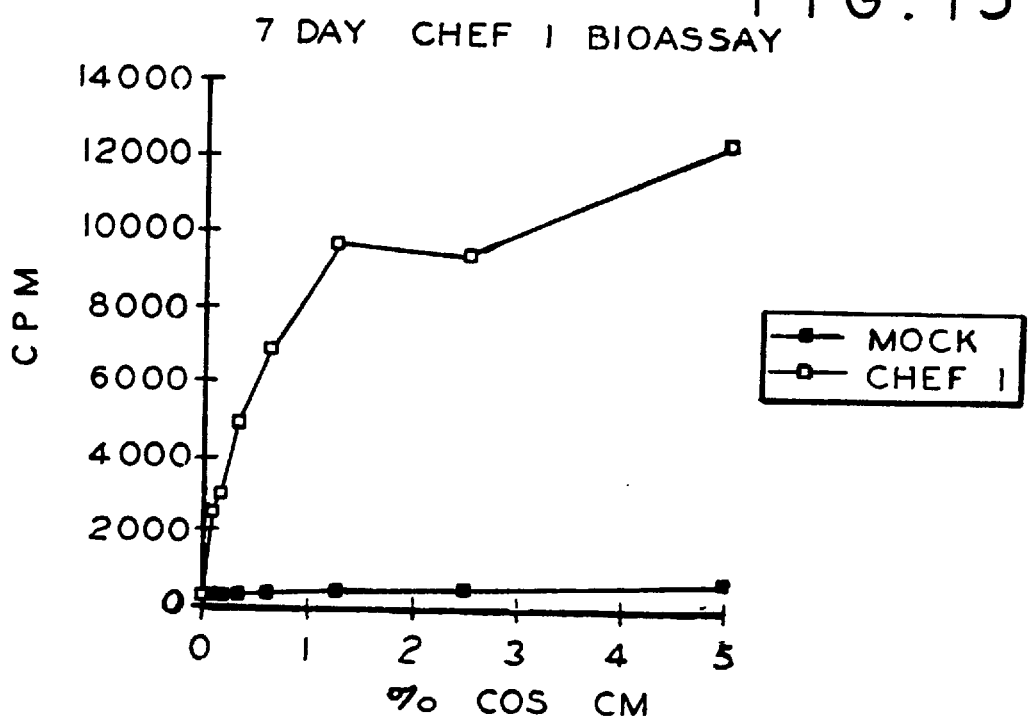
FIG. 15, illustrating results from Example 10 shows the proliferative response to COS cell supernatants containing CHEF-1 in a 7 day bioassay. The results from the 7 day proliferation show a similar approximately 10-fold increase with only 0.078% conditioned media but additional cellular activity was detected with increasing doses of CHEF-1, to approximately 40-fold with >1.25% CHEF-1 containing COS cell supernatant.

FIG. 15 shows the proliferative response to COS cell supernatants containing CHEF-1 in a 7 day bioassay. The results from the 7 day proliferation show a similar 10-fold increase with only 0.078% conditioned media but additional cellular activity was detected with increasing doses of CHEF-1, to 40-fold with >1.25% CHEF-1 containing COS cell supernatant.

EXAMPLE 11

Synergistic Combination of CHEF-3 with Porcine LIF

The stimulation of proliferation and colony formation by CHEF-3 in combination with porcine leukemia inhibitory factor (LIF) as compared to porcine LIF alone was examined. The capacity of LIF to stimulate the proliferation of porcine bone marrow cells [BMC] in a 7 day proliferation assay was tested over a dose range of 0–100 ng/ml with the results shown in FIG. 16. A 2–3 fold increase in proliferation was detected with an optimal level of stimulation detected at 50 ng/ml. When BMC were co-cultured with a constant level of CHEF-3[20% COS cell supernatant] against increasing doses of LIF, a LIF dose of 100 ng/ml stimulated >4-fold increase in cellular proliferation. These results demonstrate that LIF alone has a mild proliferative signal in culture containing serum but, when combined with CHEF-3, the response was enhanced to levels greater than the additive effect of each factor alone.

Figure 17:
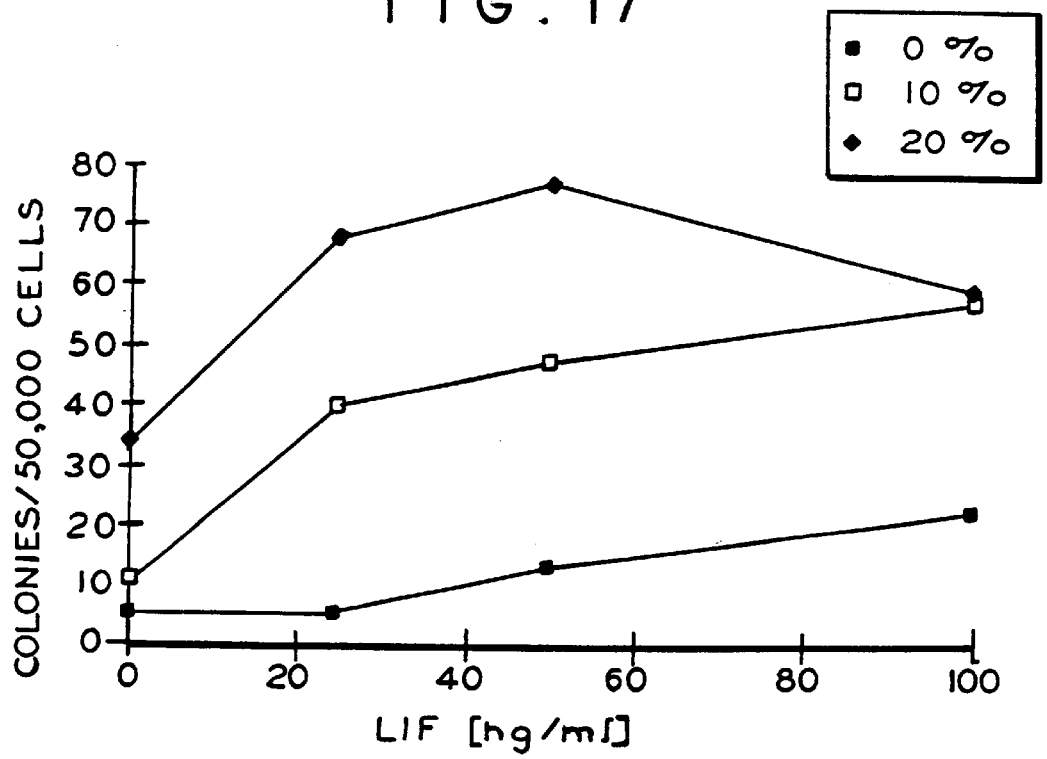

To further support this observation and to document that the combination of LIF and CHEF-3 stimulates not only proliferation but also the formation of colonies in a colony forming assay; BMC were cultured in the presence of CHEF-3 [10 and 20% COS cell supernatants] and increasing doses of LIF. The potential of these two factors to form colonies when combined is illustrated in FIG. 17. These results show that LIF alone has only minor stimulatory activity but when combined with CHEF-3, the number of colonies increased from 11 CFU to 57 CFU when 10% CHEF-3 was used and the LIF dose was increased to 100 ng/ml. A maximal number of colonies were formed in the presence of 20% CHEF-3 and 50 ng/ml LIF. These results support the observations from the proliferation assays that the combination of LIF and CHEF-3 potentiates BMC proliferation and correlates to colony formation.

The short term effect of LIF and CHEF-3 in combination with LIF on engraftment of porcine bone marrow cells (BMC) on primate bone marrow stromal cells was also investigated. The results of the proliferation and colony formation studies were further developed in long term bone marrow cultures (LTBMC) using primary cultures of preformed stromal cells from either porcine [allo] or primate [xeno] bone marrow. The effect of LIF on cellularity after one week in culture is illustrated in FIG. 18. There was a >50% increase in cellularity of pig BMC grown on xeno stromal cells in the presence of LIF when compared to cells grown in media alone; a similar but less striking increase (24%) was detected in allo-LTBMC. Cultures grown in the absence of preformed stromal cells showed a decline in cellularity in the presence of LIF. After 7 days only a small increase in the number of progenitor cells was detected in xeno-LTBMC in the presence of LIF (FIG. 19). In contrast, allo-LTBMC stimulated with LIF had a small decrease in the number progenitor cells. Cultures without preformed stromal cells showed no positive effect with LIF on progenitor cell development.

Figure 20A:
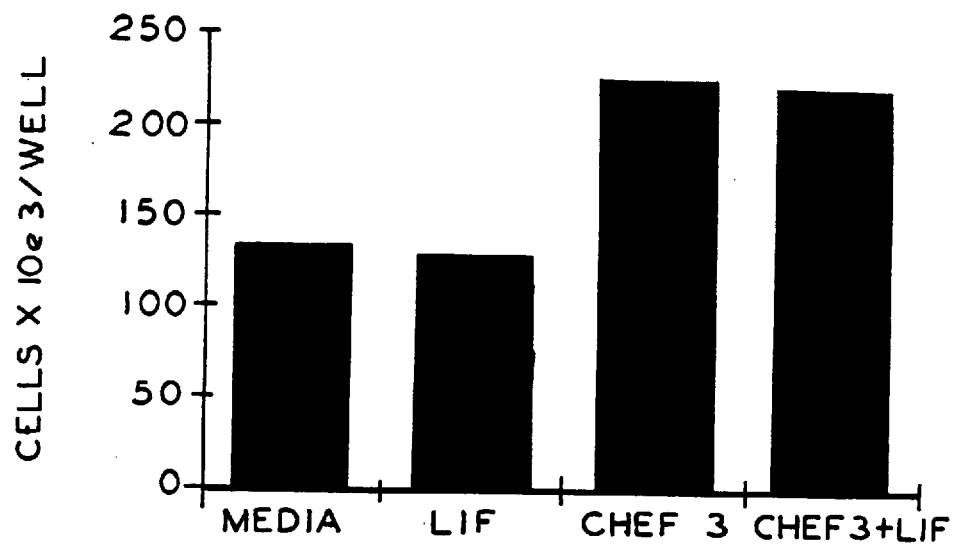

The initial studies identified that CHEF-3 in combination with LIF enhanced cell proliferation and colony formation. After one week on allo-stromal cells (FIG. 20B), a significant increase in cellularity was detected in cultures grown in the presence of CHEF-3 in combination with LIF when compared to CHEF-3 alone, 740,000 cells versus 260,000 cells, respectively. However, there was not a major difference in the cellularity between CHEF-3 and CHEF-3 plus LIF stimulated cultures when BMC were grown on xeno-stromal cells (FIG. 20A). In contrast, there was a greater number of progenitor cells detected in both the allo- (FIG. 21B) and xeno-LTBMC (FIG. 21A) cultured with CHEF-3 plus LIF than detected in cultures with CHEF-3 alone. Further, the number of progenitor cells detected in the xeno-LTBMC in the presence of CHEF-3 plus LIF was similar to the number detected in the allo-LTBMC, even though the cellularity from the xeno-LTBMC was only about 33% of that found in the allo-LTBMC (FIG. 19). These results document that a combination of CHEF-3 and LIF in either allo- or xeno-LTBMC stimulates the development of progenitor cells and extends the observation for enhanced growth on xeno bone marrow stromal cells.

The Effect of LIF and CHEF-3 plus LIF On Long Term Maintenance of Primitive Bone Marrow Cells on Xeno-Stromal Cells.

Figure 22A:
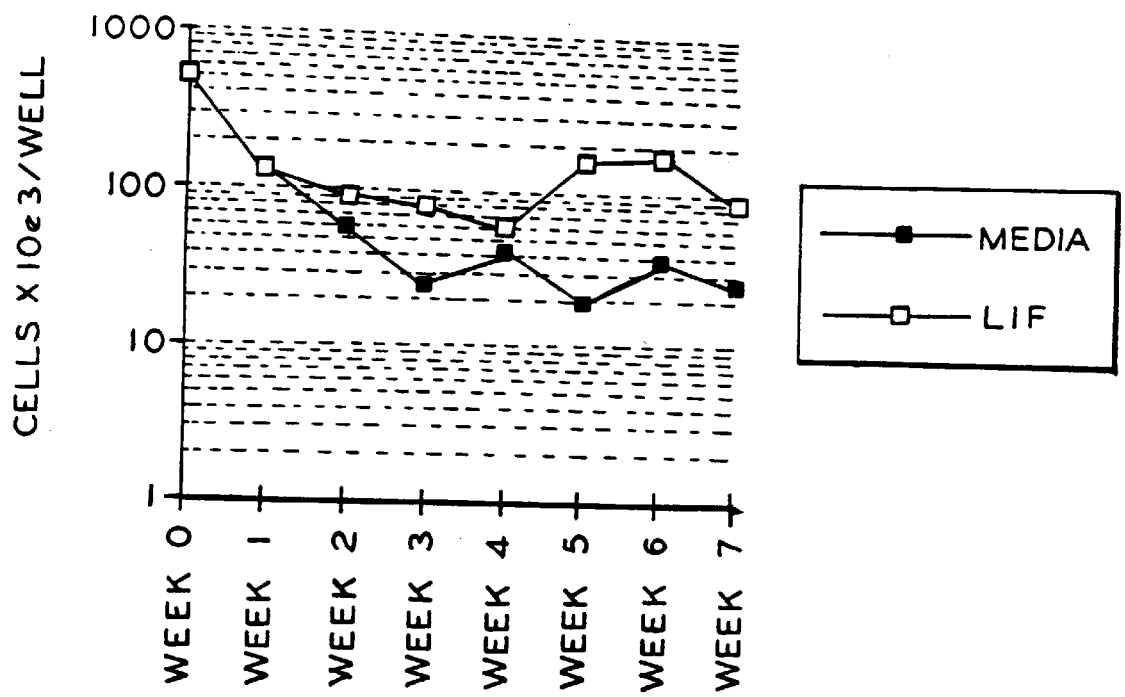
FIGS. 22A–22D. A comparative long term effect of continuous versus two weeks of added exogenous LIF to cellular and progenitor cell development in xeno-LTBMC. Primary primate stromal cells were prepared as previously described and seeded with 500,000 pig BMC. Cells were plated in either standard LTBMC media or media supplemented with LIF, [50ng/ml]. All cells from 2 wells were harvested at weekly intervals to document the development of the cultures. In panels A and B, the effect of continuous LIF (□) on cellularity (FIG. 22A) and progenitor cell development (FIG. 22B) was compared to media (■) alone. In panels C and D, LIF (□) was maintained in the cultures for only the first two weeks. After the second week, the media was replaced with standard LTBMC media. This was compared to media alone [■] for the entire culture period.
Figure 22B:
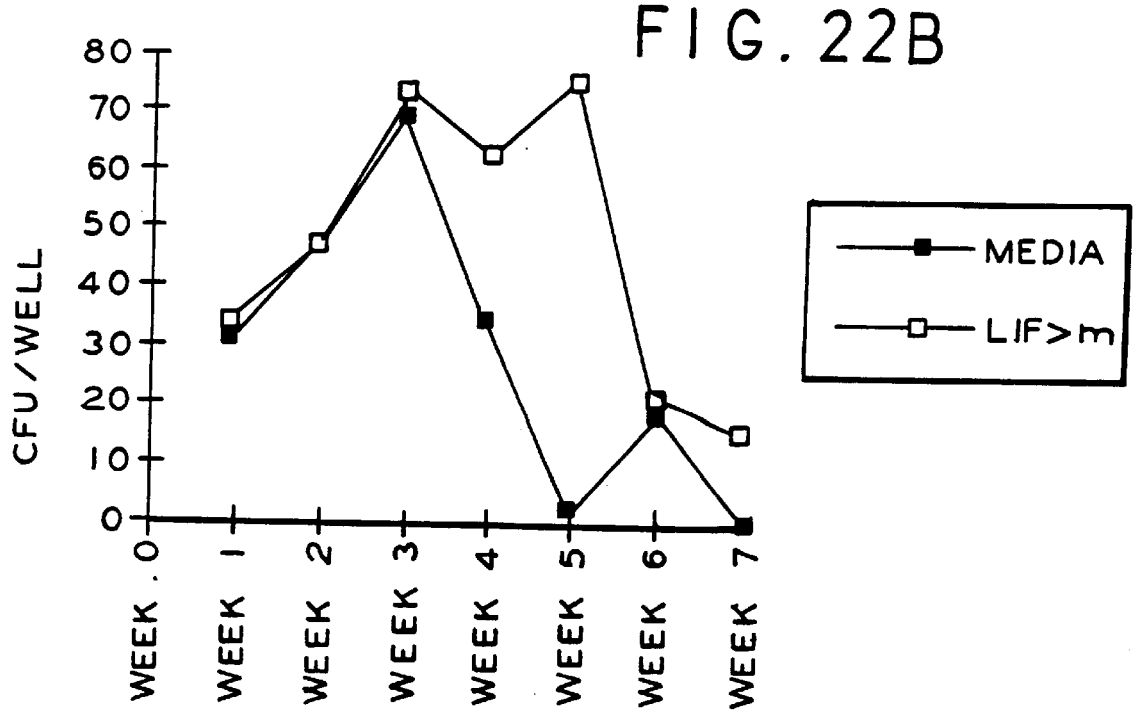
Figure 22C:
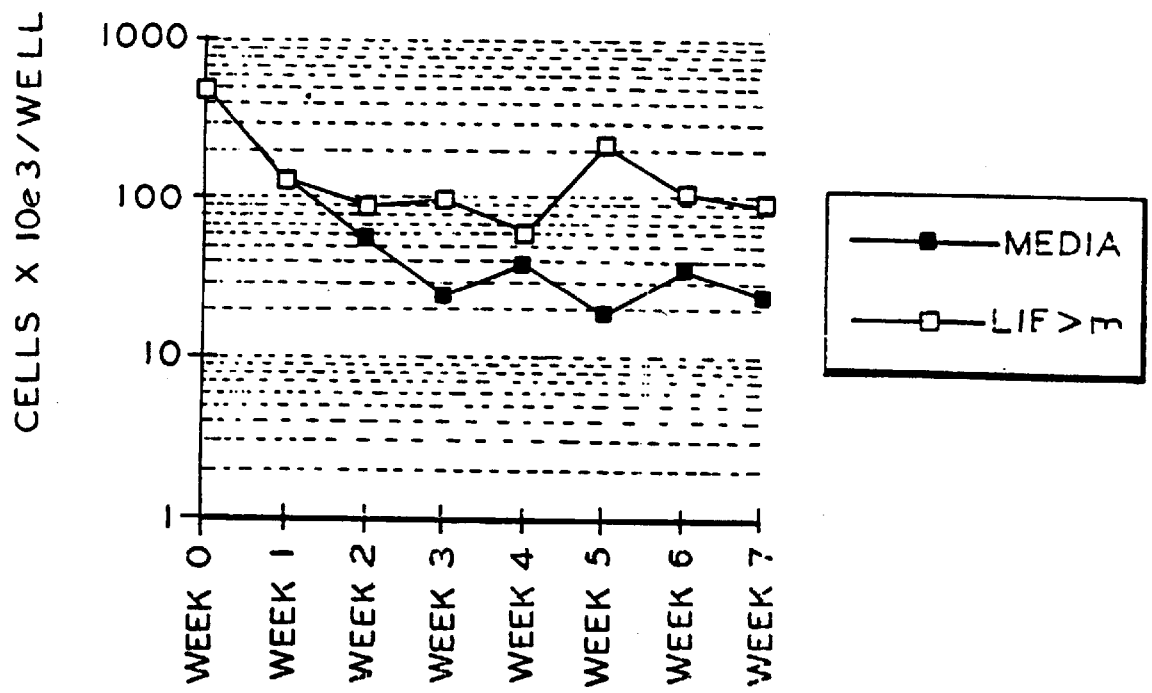
Figure 22D:
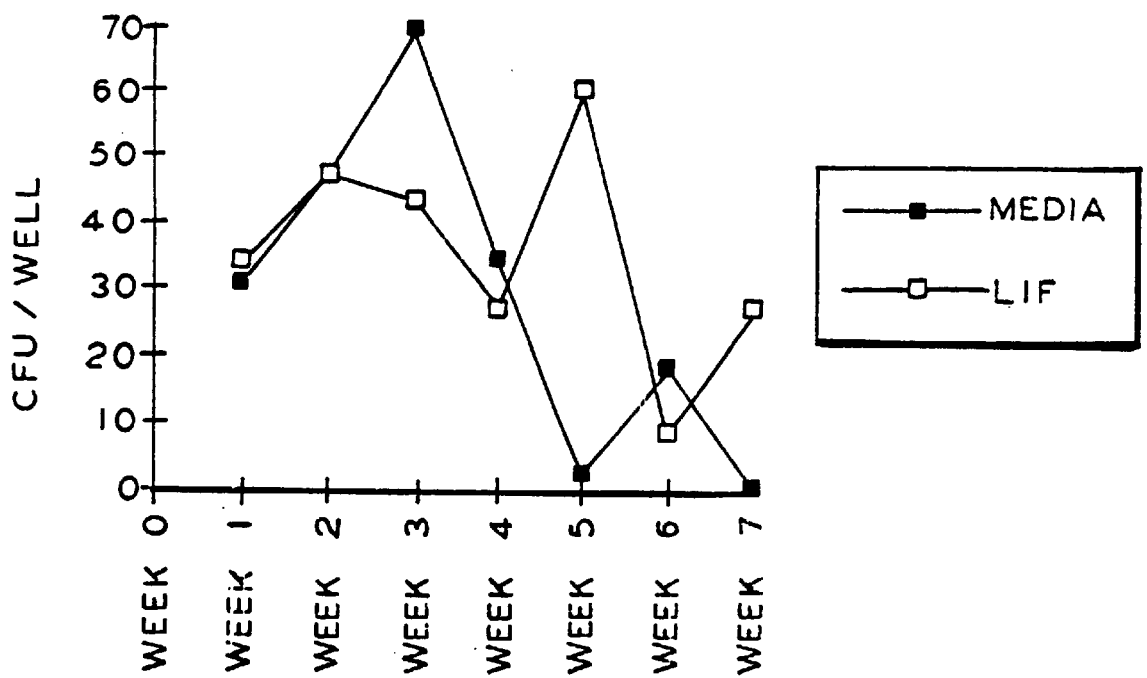

The long term effects of LIF on cellularity and generation and maintenance of progenitor cells in xeno-LTBMC are illustrated in FIGS. 22A–22D. LIF for 7 weeks in xeno-LTBMC led to a higher maintenance level of cells than observed in media controls (FIG. 22A). There was a subtle difference in the progenitor cell content between media and LIF treated cultures (FIG. 22B) where LIF treated cultures had a greater number of progenitors at weeks 5 and 7. This indicated that LIF promoted the continued long term maintenance of progenitor cells. A two week course of LIF was compared to the 7 week course and a significant effect on cellularity was not observed (FIG. 28C). Instead, there was a distinct change in the kinetics and progenitor cell content in the cultures after removing LIF from the culture media (FIG. 22D). The progenitor cell number increased through week 3 and was maintained at this level through week 5 compared to the continuous treatment with LIF (FIG. 22B). These results indicate that LIF has regulatory properties which limits the development or responsiveness of primitive cells into progenitor cells.

Figure 23A:
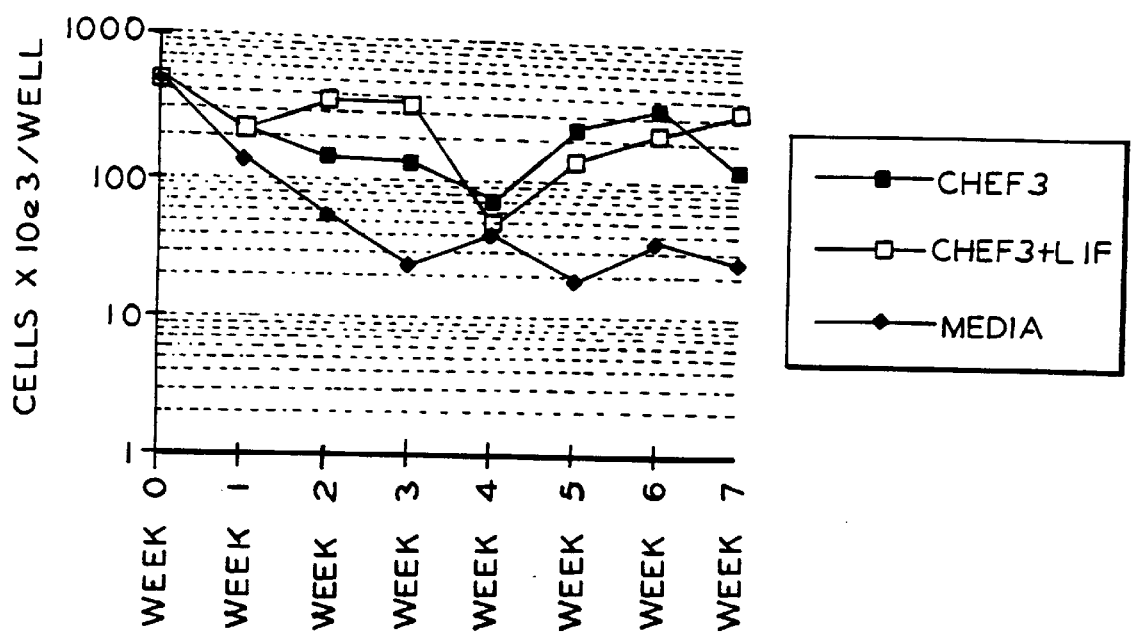
FIG. 23A & B. A comparison of the long term effect of continuous CHEF-3 or CHEF-3+LIF on the cellular and progenitor cell development in xeno-LTBMC. LTBMC were established and set up as previously described. In these experiments, the effects standard LTBMC media (♦) were compared to CHEF-3 (20% COS cell supernatant; ■) or CHEF-3 [20%] and LIF [50ng/ml] (□). Documentation of the development of the LTBMC was as previously described.
Figure 23B:
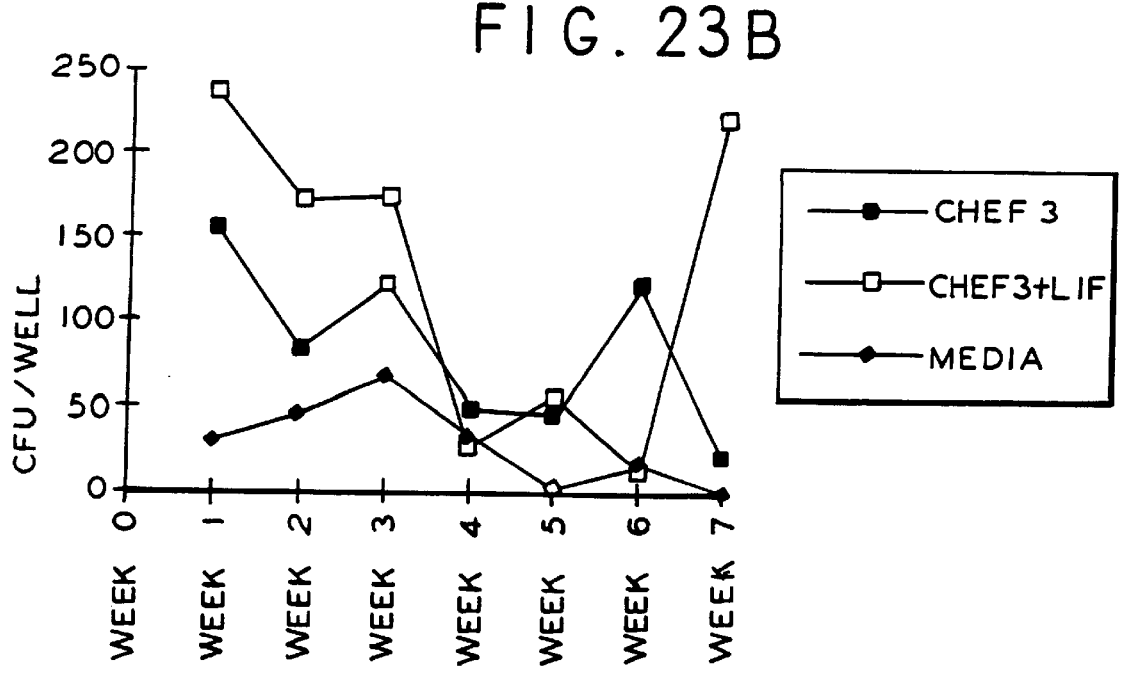

Xeno-LTBMC grown in the presence of a combination of CHEF-3 and LIF had a greater cellular and progenitor cell production over a 7 week culture period than what was observed for LTBMC treated with CHEF-3 along (FIG. 23). A striking feature of these results was the higher number of cells and progenitor cells at weeks 2 and 3 in the cultures stimulated with CHEF-3 plus LIF. There was a decrease in cellularity and progenitor cell content on week 4 which was followed by a steady increase in cellularity and a dramatic rebound in the progenitor cell level at week 7. These results identify two valuable facets of this LIF plus CHEF-3 combination, the first is the ability to enhance cellular and progenitor cell production; and the second is to favor long term engraftment in a xeno-stromal environment. This later interpretation is supported by the strong recovery of cellularity and progenitor cell content after 7 weeks in culture. Cells found at week 7 in CHEF-3 plus LIF cultures were blasts and immature cells of the granulocytic lineage, suggesting active proliferation while the cells obtained from other culture conditions were predominantly macrophages, characteristic of terminal cultures.

Figure 16:
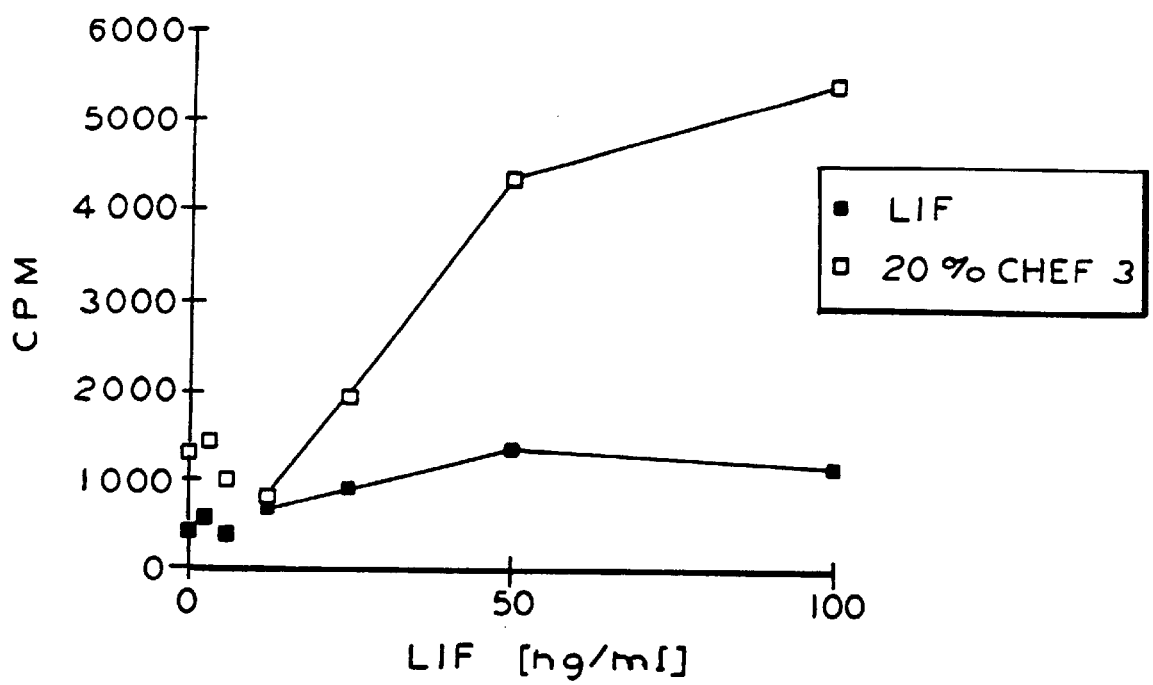

FIG. 16. Effect of LIF and LIF plus CHEF-3 on the proliferation of pig BMC. Pig BMC were plated at a concentration of 10,000 cells/well in 96 well round bottomed tissue culture plates in Iscove's media containing 10% fetal bovine serum [FBS] (total volume/well 200 ul). To one series of wells LIF was added over a series of dilutions of 0–100 ng/ml (■). To a second series of wells, media was made 20% with a COS cell supernatant containing CHEF-3 and the dilution of LIF was added (□). Cultures were grown at 37° C., 5% $CO_2$, for 7 days. On the 6th day of culture, 1 mCi of $^3$H-Tdr was added; cells from the plates were harvested on day 7 using a Tomtec Harvester and radioactivity was counted using a Beta-plate reader. Each data point is the mean of three wells.

FIG. 17. Effect of LIF and CHEF-3 on colony formation. Pig BMC (25,000 cells/ml) were set up in cultures containing CHEF-3 (doses 0 (■), 10 (□), and 20% (♦) COS cell supernatants) with dose titrations of LIF (0,25,50 and 100 ng/ml) in Iscove's media containing 30% FBS and made 1.1% in methylcellulose. 1 ml volumes were plated in duplicate and cultured for 14 days at 37° C., 5% $CO_2$. Colonies were enumerated as having greater than 50 cells.

FIGS. 18 and 19. Effect of LIF and either primary allo-or xeno-stromal cells on cellularity (FIG. 18) and progenitor cell development (FIG. 19) after 1 week in culture. Primary stromal cells were established after 3 weeks in culture from either primate [xeno-sc] or porcine [allo-sc] BMC seeded in 24 well plates at $2\times10^6$ cells/ml in media 199 containing 10% FBS, 10% horse serum and $10^{-6}$M hydrocortisone [standard LTBMC media]. Media was changed weekly and the nonadherent cell population was demi-depleted. After development of a stromal layer, the primary cells were irradiated with 10 Gy, media was changed then each well was seeded with 500,000 pig BMC. Control cultures [no sc] did not contain any preformed stromal elements. The variable was either media or media containing LIF, 50 ng/ml. At the end of 7 days, the adherent and nonadherent cells were harvested from 3 wells and the number of cells per well was determined. An aligout of cells from each well was plated in methylcellulose cultures containing 10% PHA-LCM, 2 U/ml erythropoietin, 30% FBS in Iscove's media to determine colony forming units. Colonies were counted after 14 days in culture with criteria as previously descibed. The plotted results are the mean of three separate experiments.

Figure 20B:
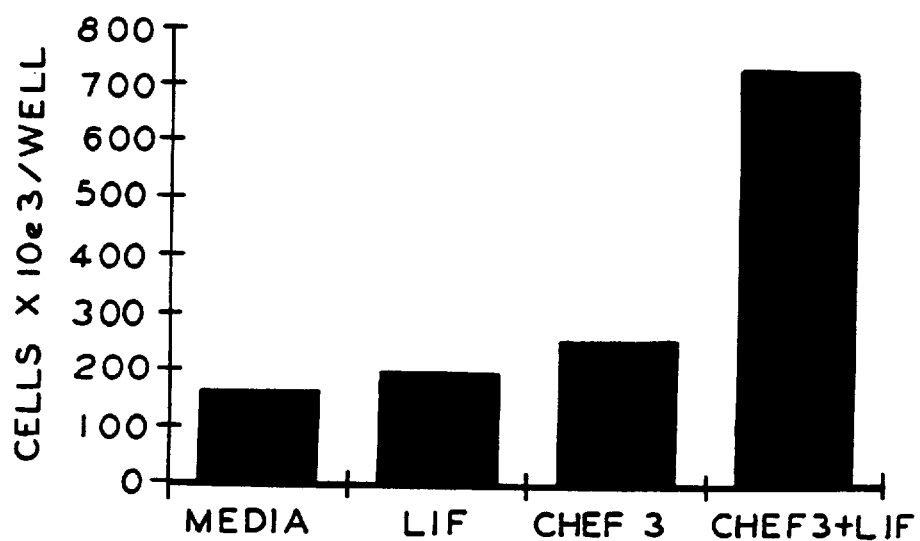
Figure 21A:
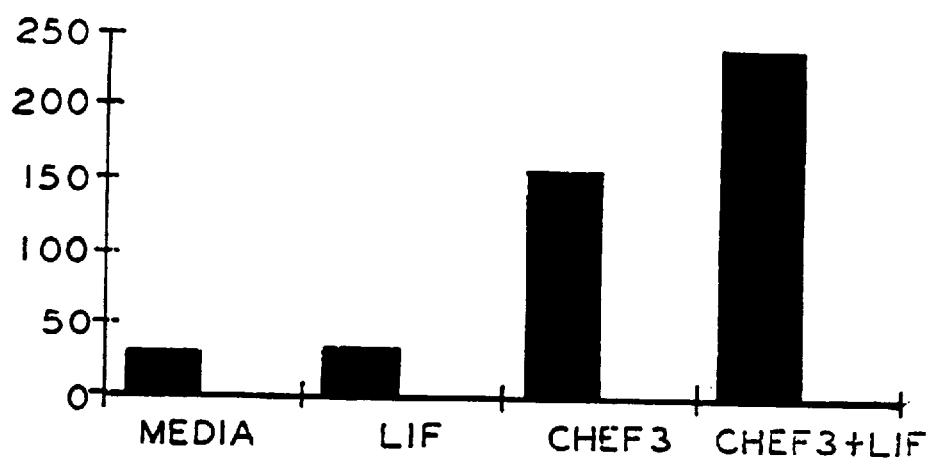
Figure 21B:
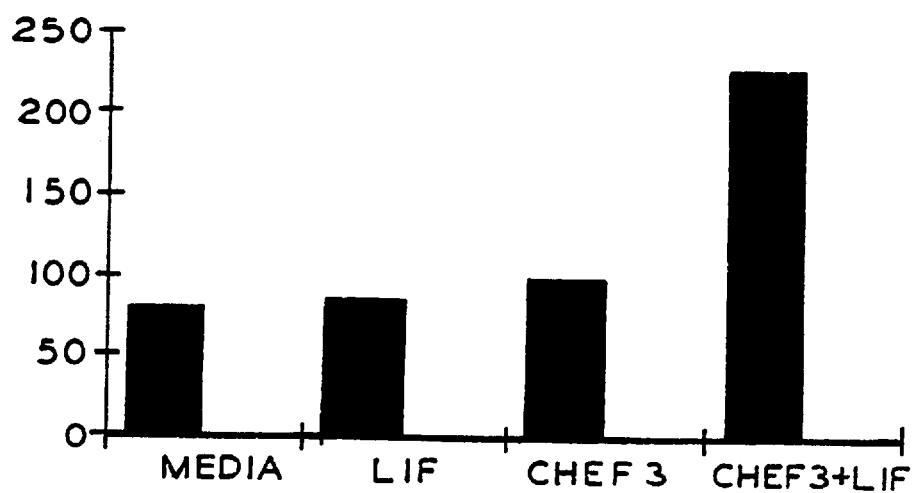

FIGS. 20 and 21. Effect of LIF, CHEF-3, or LIF+CHEF-3 and either primary allo- or xeno-stromal cells on cellularity (FIG. 20A and 20B) and progenitor cell development (FIGS. 21A and 21B) after 1 week in culture. Cultures were established as described in detail in the legend for FIG. 18. The variable is the addition of either LIF [50 ng/ml], CHEF-3 [20% COS cell supernatant] or the combination of both to standard LTBMC media. At the end of 7 days, all cells from 2 wells were harvested, cell number was determined and an aliquot of cells was plated in a colony forming assay.

FIGS. 22A–22D. A comparative long term effect of continuous versus two weeks of exogenous LIF to cellular and progenitor cell development in xeno-LTBMC. Primary primate stromal cells were prepared as previously described and seeded with 500,000 pig BMC. Cells were plated in either standard LTBMC or media containing LIF, 50 ng/ml. LTBMC were maintained by weekly feeding of the cultures using the appropriate media. All cells from 2 wells were harvested at weekly intervals to document the development of the cultures. In panels A and B, the effect of continuous LIF (□) on cellularity and progenitor cell development was compared to media (■) alone. In panels C and D, LIF (□) was maintained in the cultures for only the first two weeks. After the second week, the media was replaced with standard LTBMC media. This was compared to media alone (■) for the entire culture period.

FIG. 23. A comparison of the long term effect of continuous CHEF-3 or CHEF-3 +LIF on the cellular and progenitor cell development in xeno-LTBMC. LTBMC were established and set up as previously described. In these experiments, standard LTBMC media was supplemented with CHEF3 [20% COS cell supernatant] or CHEF-3 [20%] and LIF [50 ng/ml]. Documentation of the development of the LTBMC was as previously described.

What is claimed is:

1. A method for increasing the survival of porcine bone marrow cells in a primate, comprising:
administering to a primate porcine bone marrow cells and at least one porcine cytokine, said porcine cytokine being provided in an amount effective to increase survival of said porcine bone marrow cells, said porcine cytokine being a member selected from the group consisting of (i) a polypeptide comprising amino acid 1 to amino acid 180 of SEQ ID NO: 4, and conservative substitution and deletion variants thereof having porcine stem cell factor activity which increases survival of porcine bone marrow cells, (ii) a polypeptide comprising amino acids 1 to 127 of SEQ ID NO: 11 and conservative substitution and deletion variants thereof having porcine GM-CSF activity which increases survival of porcine bone marrow cells; and (iii) a polypeptide comprising amino acids 1 to 121 of SEQ ID NO: 21 and conservative substitution and deletion variants thereof having porcine IL-3 activity which increases survival of porcine bone marrow cells.

2. The method of claim 1 wherein said at least one porcine cytokine is a polypeptide comprising amino acid 1 to amino acid 180 of SEQ ID NO. 4.

3. The method of claim 1 wherein said at least one porcine cytokine is a polypeptide comprising amino acids 1 to 127 of SEQ ID NO. 11.

4. The method of claim 1 wherein said at least one porcine cytokine is a polypeptide comprising amino acids 1 to 121 of SEQ ID NO. 21.

5. The method of claim 1 wherein the primate is administered with a polypeptide comprising amino acid 1 to amino acid 180 of SEQ ID NO. 4 and a polypeptide comprising amino acids 1 to 127 of SEQ ID NO. 11.

6. The method of claim 1 wherein the primate is administered with a polypeptide comprising amino acids 1 to 180 of SEQ ID NO. 4 and a polypeptide comprising amino acid 1 to 121 of SEQ ID NO. 21.

7. The method of claim 1 wherein the primate is administered with a polypeptide comprising amino acids 1 to 127 of SEQ ID NO. 11 and a polypeptide comprising amino acids 1 to 121 of SEQ ID NO. 21.

8. The process of claim 1 wherein the primate is treated with a polypeptide comprising amino acids 1 to 180 of SEQ ID NO. 4, a polypeptide comprising amino acids 1 to 127 of SEQ ID NO. 11, and a polypeptide comprising amino acids 1 to 121 of SEQ ID NO. 21.

9. The method of claim 1 wherein the at least one porcine cytokine is administered in an amount from about 20 micrograms per kilogram to about 100 micrograms per kilogram of recipient's body weight.

10. The method of claim 1 wherein the at least one porcine cytokine is administered in an amount from about 5 micrograms per kilogram to about 500 micrograms per kilogram of recipient's body weight.

* * * * *

UNITED STATES PATENT AND TRADEMARK OFFICE
CERTIFICATE OF CORRECTION

PATENT NO. : 5,858,963
DATED : January 12, 1999
INVENTOR(S) : Robert J. Hawley, et al It is certified that error appears in the above-identified patent and that said Letters Patent is hereby corrected as shown below:

On the title page, item [75] change "Ronath" to --Ponath--.

At column 2, line 17, delete the hyphen.

At column 2, line 65, change "granulocyle" to --granulocyte--.

At column 14, line 57, change "$2x10^6$ ml" to --$2x10^6$/ml--.

At column 15, line 3, change "$32x10^3$ ml" to --$32x10^3$/ml--.

At column 20, line 48, change "Z18291" to --X53561--.

At column 21, line 63, change "aliquol" to --aliquot--.

At column 28, line 67, change "aligout" to --aliquot--.

At column 29, line 4, change "descibed" to --described--.

Signed and Sealed this

Twentieth Day of July, 1999

Attest:

*Attesting Officer*

Q. TODD DICKINSON

*Acting Commissioner of Patents and Trademarks*

SEQUENCE LISTING ( 1 ) GENERAL INFORMATION:

( i i i ) NUMBER OF SEQUENCES: 24

( 2 ) INFORMATION FOR SEQ ID NO: 1:

( i ) SEQUENCE CHARACTERISTICS:
        ( A ) LENGTH: 21 BASES
        ( B ) TYPE: NUCLEIC ACID
        ( C ) STRANDEDNESS: SINGLE
        ( D ) TOPOLOGY: LINEAR ( i i i ) HYPOTHETICAL: NO ( i v ) ANTI-SENSE: NO ( x i ) SEQUENCE DESCRIPTION: SEQ ID NO: 1:

```
          GCGCTGCCTT  TCCTTATGAA  G                          21
```

( 2 ) INFORMATION FOR SEQ ID NO: 2:

( i ) SEQUENCE CHARACTERISTICS:
        ( A ) LENGTH: 24 BASES
        ( B ) TYPE: NUCLEIC ACID
        ( C ) STRANDEDNESS: SINGLE
        ( D ) TOPOLOGY: LINEAR ( i i i ) HYPOTHETICAL: NO ( i v ) ANTI-SENSE: YES ( x i ) SEQUENCE DESCRIPTION: SEQ ID NO: 2:

```
          TTAGGCTTTC  CTATTACTGC  TACT                       24
```

( 2 ) INFORMATION FOR SEQ ID NO: 3:

( i ) SEQUENCE CHARACTERISTICS:
        ( A ) LENGTH: 633 BASE PAIRS
        ( B ) TYPE: NUCLEIC ACID
        ( C ) STRANDEDNESS: DOUBLE
        ( D ) TOPOLOGY: LINEAR ( i i i ) HYPOTHETICAL: NO ( i v ) ANTI-SENSE: NO ( x i ) SEQUENCE DESCRIPTION: SEQ ID NO: 3:

```
                                                    GCGCT GCCTTTCCTT                    15

ATG AAG AAG ACA CAA ACT TGG ATT ATC ACT TGC ATT TAT CTT CAA CTG    63
Met Lys Lys Thr Gln Thr Trp Ile Ile Thr Cys Ile Tyr Leu Gln Leu
-25             -20                 -15                 -10

CTC CTA TTT AAT CCT CTC GTC AGA ACT CAA GGG ATC TGC AGG AAC CGT    111
Leu Leu Phe Asn Pro Leu Val Arg Thr Gln Gly Ile Cys Arg Asn Arg
            -5                  1                   5

GTG ACT GAT GAT GTG AAA GAC GTT ACA AAA TTG GTG GCA AAT CTT CCA    159
Val Thr Asp Asp Val Lys Asp Val Thr Lys Leu Val Ala Asn Leu Pro
        10              15                  20

AAA GAC TAT AAG ATA ACC CTC AAA TAT GTC CCC GGG ATG GAC GTT TTG    207
Lys Asp Tyr Lys Ile Thr Leu Lys Tyr Val Pro Gly Met Asp Val Leu
    25              30              35

CCT AGT CAT TGT TGG ATA AGC GAA ATG GTG GAA CAA CTG TCA GTC AGC    255
Pro Ser His Cys Trp Ile Ser Glu Met Val Glu Gln Leu Ser Val Ser
40              45                  50              55

TTG ACT GAT CTT CTG GAC AAG TTT TCC AAT ATT TCT GAA GGC TTG AGT    303
Leu Thr Asp Leu Leu Asp Lys Phe Ser Asn Ile Ser Glu Gly Leu Ser
                60              65              70

AAT TAT TCT ATC ATA GAC AAA CTT GTG AAA ATT GTT GAT GAC CTC GTG    351
Asn Tyr Ser Ile Ile Asp Lys Leu Val Lys Ile Val Asp Asp Leu Val
            75              80              85

GAA TGC ATG GAA GAA CAC TCA TTT GAG AAT GTA AGA AAA TCA TCT AAG    399
Glu Cys Met Glu Glu His Ser Phe Glu Asn Val Arg Lys Ser Ser Lys
        90              95                  100

AGC CCA GAA CCC AGG CTG TTT ACT CCT GAA AAA TTC TTT GGG ATT TTT    447
Ser Pro Glu Pro Arg Leu Phe Thr Pro Glu Lys Phe Phe Gly Ile Phe
    105             110             115

AAT AGA TCC ATC GAT GCC TTC AAG GAT TTG GAG ATG GTG GCA CCT AAA    495
Asn Arg Ser Ile Asp Ala Phe Lys Asp Leu Glu Met Val Ala Pro Lys
120             125             130             135

ACT AGT GAA TGT GTG ATT TCT TCA ACA TTA ACT CCT GAA AAA GAT TCC    543
Thr Ser Glu Cys Val Ile Ser Ser Thr Leu Thr Pro Glu Lys Asp Ser
            140             145             150

AGA GTC AGT GTC ACA AAA CCA TTT ATG TTA CCC CCT GTT GCA GCC AGC    591
Arg Val Ser Val Thr Lys Pro Phe Met Leu Pro Pro Val Ala Ala Ser
        155             160             165

TCC CTT AGG AAT GAC AGC AGT AGC AGT AAT AGG AAA GCC TAA            633
Ser Leu Arg Asn Asp Ser Ser Ser Ser Asn Arg Lys Ala
            170             175             180
```

( 2 ) INFORMATION FOR SEQ ID NO: 4:

( i ) SEQUENCE CHARACTERISTICS:
        ( A ) LENGTH: 205 AMINO ACIDS
        ( B ) TYPE: AMINO ACID
        ( C ) STRANDEDNESS: SINGLE
        ( D ) TOPOLOGY: LINEAR ( i i i ) HYPOTHETICAL: YES ( i v ) ANTI-SENSE: NO ( x i ) SEQUENCE DESCRIPTION: SEQ ID NO: 4:

```
Met Lys Lys Thr Gln Thr Trp Ile Ile Thr Cys Ile Tyr Leu Gln Leu
-25             -20                 -15                 -10

Leu Leu Phe Asn Pro Leu Val Arg Thr Gln Gly Ile Cys Arg Asn Arg
            -5                  1                   5

Val Thr Asp Asp Val Lys Asp Val Thr Lys Leu Val Ala Asn Leu Pro
        10              15                  20
```

| Lys | Asp | Tyr | Lys | Ile | Thr | Leu | Lys | Tyr | Val | Pro | Gly | Met | Asp | Val | Leu |
|---|---|---|---|---|---|---|---|---|---|---|---|---|---|---|---|
| | 25 | | | | 30 | | | | | 35 | | | | | |

| Pro | Ser | His | Cys | Trp | Ile | Ser | Glu | Met | Val | Glu | Gln | Leu | Ser | Val | Ser |
|---|---|---|---|---|---|---|---|---|---|---|---|---|---|---|---|
| 40 | | | | | 45 | | | | 50 | | | | | | 55 |

| Leu | Thr | Asp | Leu | Leu | Asp | Lys | Phe | Ser | Asn | Ile | Ser | Glu | Gly | Leu | Ser |
|---|---|---|---|---|---|---|---|---|---|---|---|---|---|---|---|
| | | | | 60 | | | | | 65 | | | | | 70 | |

| Asn | Tyr | Ser | Ile | Ile | Asp | Lys | Leu | Val | Lys | Ile | Val | Asp | Asp | Leu | Val |
|---|---|---|---|---|---|---|---|---|---|---|---|---|---|---|---|
| | | | 75 | | | | | 80 | | | | | 85 | | |

| Glu | Cys | Met | Glu | Glu | His | Ser | Phe | Glu | Asn | Val | Arg | Lys | Ser | Ser | Lys |
|---|---|---|---|---|---|---|---|---|---|---|---|---|---|---|---|
| | | 90 | | | | | 95 | | | | | 100 | | | |

| Ser | Pro | Glu | Pro | Arg | Leu | Phe | Thr | Pro | Glu | Lys | Phe | Phe | Gly | Ile | Phe |
|---|---|---|---|---|---|---|---|---|---|---|---|---|---|---|---|
| | 105 | | | | | 110 | | | | | 115 | | | | |

| Asn | Arg | Ser | Ile | Asp | Ala | Phe | Lys | Asp | Leu | Glu | Met | Val | Ala | Pro | Lys |
|---|---|---|---|---|---|---|---|---|---|---|---|---|---|---|---|
| 120 | | | | | 125 | | | | | 130 | | | | | 135 |

| Thr | Ser | Glu | Cys | Val | Ile | Ser | Ser | Thr | Leu | Thr | Pro | Glu | Lys | Asp | Ser |
|---|---|---|---|---|---|---|---|---|---|---|---|---|---|---|---|
| | | | | 140 | | | | | 145 | | | | | 150 | |

| Arg | Val | Ser | Val | Thr | Lys | Pro | Phe | Met | Leu | Pro | Pro | Val | Ala | Ala | Ser |
|---|---|---|---|---|---|---|---|---|---|---|---|---|---|---|---|
| | | | 155 | | | | | 160 | | | | | 165 | | |

| Ser | Leu | Arg | Asn | Asp | Ser | Ser | Ser | Asn | Arg | Lys | Ala | | | | |
|---|---|---|---|---|---|---|---|---|---|---|---|---|---|---|---|
| | | 170 | | | | | 175 | | | | 180 | | | | |

( 2 ) INFORMATION FOR SEQ ID NO: 5:

( i ) SEQUENCE CHARACTERISTICS:
        ( A ) LENGTH: 10 BASES
        ( B ) TYPE: NUCLEIC ACID
        ( C ) STRANDEDNESS: SINGLE
        ( D ) TOPOLOGY: LINEAR ( i i i ) HYPOTHETICAL: NO ( i v ) ANTI-SENSE: NO ( x i ) SEQUENCE DESCRIPTION: SEQ ID NO: 5:

CGGAATTCCG    10

( 2 ) INFORMATION FOR SEQ ID NO: 6:

( i ) SEQUENCE CHARACTERISTICS:
        ( A ) LENGTH: 18 BASES
        ( B ) TYPE: NUCLEIC ACID
        ( C ) STRANDEDNESS: SINGLE
        ( D ) TOPOLOGY: LINEAR ( i i i ) HYPOTHETICAL: NO ( i v ) ANTI-SENSE: NO ( x i ) SEQUENCE DESCRIPTION: SEQ ID NO: 6:

GATCACAAGG GATCTGCA    18

( 2 ) INFORMATION FOR SEQ ID NO: 7:

( i ) SEQUENCE CHARACTERISTICS:
        ( A ) LENGTH: 10 BASES
        ( B ) TYPE: NUCLEIC ACID
        ( C ) STRANDEDNESS: SINGLE
        ( D ) TOPOLOGY: LINEAR ( i i i ) HYPOTHETICAL: NO ( i v ) ANTI-SENSE: YES ( x i ) SEQUENCE DESCRIPTION: SEQ ID NO: 7:

GATCCCTTGT    10

( 2 ) INFORMATION FOR SEQ ID NO: 8:

( i ) SEQUENCE CHARACTERISTICS:
        ( A ) LENGTH: 21 BASES
        ( B ) TYPE: NUCLEIC ACID
        ( C ) STRANDEDNESS: SINGLE
        ( D ) TOPOLOGY: LINEAR ( i i i ) HYPOTHETICAL: NO ( i v ) ANTI-SENSE: NO ( x i ) SEQUENCE DESCRIPTION: SEQ ID NO: 8:

```
          TTGGGCACTG TGGCCTGCAG C                                    21
```

( 2 ) INFORMATION FOR SEQ ID NO: 9:

( i ) SEQUENCE CHARACTERISTICS:
        ( A ) LENGTH: 21 BASES
        ( B ) TYPE: NUCLEIC ACID
        ( C ) STRANDEDNESS: SINGLE
        ( D ) TOPOLOGY: LINEAR ( i i i ) HYPOTHETICAL: NO ( i v ) ANTI-SENSE: YES ( x i ) SEQUENCE DESCRIPTION: SEQ ID NO: 9:

```
          ACAGGAAGTT TCCGGGGTTG G                                    21
```

( 2 ) INFORMATION FOR SEQ ID NO: 10:

( i ) SEQUENCE CHARACTERISTICS:
        ( A ) LENGTH: 798 BASE PAIRS
        ( B ) TYPE: NUCLEIC ACID
        ( C ) STRANDEDNESS: DOUBLE
        ( D ) TOPOLOGY: LINEAR ( i i i ) HYPOTHETICAL: NO ( i v ) ANTI-SENSE: NO ( x i ) SEQUENCE DESCRIPTION: SEQ ID NO: 10:

```
GGCCGCTAA  AGGCTAAAGT  CCTCAGAAGG  ATG  TGG  CTG  CAG  AAC  CTG  CTT  CTC  CTG    56
                                   Met  Trp  Leu  Gln  Asn  Leu  Leu  Leu  Leu
                                        -15                           -10

GGC  ACT  GTG  GTC  TGC  AGC  ATC  TCC  GCT  CCC  ACC  CGC  CCA  CCC  AGC  CCT   104
Gly  Thr  Val  Val  Cys  Ser  Ile  Ser  Ala  Pro  Thr  Arg  Pro  Pro  Ser  Pro
               -5                         1                   5

GTC  ACC  CGG  CCC  TGG  CAG  CAT  GTG  GAT  GCC  ATC  AAA  GAA  GCC  CTG  AGC   152
Val  Thr  Arg  Pro  Trp  Gln  His  Val  Asp  Ala  Ile  Lys  Glu  Ala  Leu  Ser
     10                        15                       20

CTT  CTA  AAC  AAC  AGT  AAT  GAC  ACA  GCG  GCT  GTG  ATG  AAT  GAA  ACC  GTA   200
Leu  Leu  Asn  Asn  Ser  Asn  Asp  Thr  Ala  Ala  Val  Met  Asn  Glu  Thr  Val
25                       30                      35                       40

GAC  GTC  GTC  TGT  GAA  ATG  TTT  GAC  CCC  CAG  GAG  CCG  ACA  TGC  GTG  CAG   248
Asp  Val  Val  Cys  Glu  Met  Phe  Asp  Pro  Gln  Glu  Pro  Thr  Cys  Val  Gln
                    45                      50                      55

ACT  CGC  CTG  AAC  CTG  TAC  AAG  CAG  GGC  CTG  CGG  GGC  AGC  CTC  ACT  AGG   296
Thr  Arg  Leu  Asn  Leu  Tyr  Lys  Gln  Gly  Leu  Arg  Gly  Ser  Leu  Thr  Arg
               60                      65                      70

CTC  AAG  AGC  CCC  TTG  ACT  CTG  TTG  GCC  AAG  CAC  TAT  GAG  CAG  CAC  TGC   344
Leu  Lys  Ser  Pro  Leu  Thr  Leu  Leu  Ala  Lys  His  Tyr  Glu  Gln  His  Cys
          75                      80                      85

CCC  CTC  ACC  GAG  GAA  ACT  TCC  TGT  GAA  ACC  CAG  TCT  ATC  ACC  TTC  AAA   392
Pro  Leu  Thr  Glu  Glu  Thr  Ser  Cys  Glu  Thr  Gln  Ser  Ile  Thr  Phe  Lys
```

```
                    90                          95                      100
AGT  TTC  AAA  GAC  AGT  CTG  AAC  AAA  TTT  CTT  TTT  ACC  ATC  CCC  TTT  GAC        440
Ser  Phe  Lys  Asp  Ser  Leu  Asn  Lys  Phe  Leu  Phe  Thr  Ile  Pro  Phe  Asp
105                      110                 115                           120

TGC  TGG  GGG  CCA  GTC  AAA  AAG  TAA  AGCAGCTGC  AGCAGCCAGA  AGCCAGCCTT             494
Cys  Trp  Gly  Pro  Val  Lys  Lys
                    125

GCCGCACGGA  TTGCTCCCAC  TGACAGAGCC  AAACCAAACT  CAGGATCTTC  ACCGTGGAGG                554

GACCACTGGC  TGGCCAAGGC  TGTAATGGGG  CACAGACTTG  CCCTGGGCCA  TGTTGACCCT                614

GATACAGGCC  TGGCAGGGGA  AATGGCAGAT  GTTTTATACC  GGCAGGGATT  AGCAATATTT                674

ATTAACCTAT  TTATGTATTT  TAATATTTAT  TTATTTATTT  ATCTATTTAT  TTATTTAAGC                734

TTGAACTTCA  TATTTATTCA  AGATGTTTTA  CCATAATAAT  AAATTATTTA  AAATAGCGGC                794

CGCT                                                                                  798
```

( 2 ) INFORMATION FOR SEQ ID NO: 11:

( i ) SEQUENCE CHARACTERISTICS:
        ( A ) LENGTH: 144 AMINO ACIDS
        ( B ) TYPE: AMINO ACID
        ( C ) STRANDEDNESS: SINGLE
        ( D ) TOPOLOGY: LINEAR ( i i i ) HYPOTHETICAL: YES ( i v ) ANTI-SENSE: NO ( x i ) SEQUENCE DESCRIPTION: SEQ ID NO: 11:

```
                                      Met  Trp  Leu  Gln  Asn  Leu  Leu  Leu  Leu
                                           -15                      -10

Gly  Thr  Val  Val  Cys  Ser  Ile  Ser  Ala  Pro  Thr  Arg  Pro  Ser  Pro
                -5                      1                     5

Val  Thr  Arg  Pro  Trp  Gln  His  Val  Asp  Ala  Ile  Lys  Glu  Ala  Leu  Ser
          10                      15                      20

Leu  Leu  Asn  Asn  Ser  Asn  Asp  Thr  Ala  Ala  Val  Met  Asn  Glu  Thr  Val
25                      30                      35                      40

Asp  Val  Val  Cys  Glu  Met  Phe  Asp  Pro  Gln  Glu  Pro  Thr  Cys  Val  Gln
               45                      50                           55

Thr  Arg  Leu  Asn  Leu  Tyr  Lys  Gln  Gly  Leu  Arg  Gly  Ser  Leu  Thr  Arg
               60                      65                      70

Leu  Lys  Ser  Pro  Leu  Thr  Leu  Leu  Ala  Lys  His  Tyr  Glu  Gln  His  Cys
          75                      80                      85

Pro  Leu  Thr  Glu  Glu  Thr  Ser  Cys  Glu  Thr  Gln  Ser  Ile  Thr  Phe  Lys
     90                      95                      100

Ser  Phe  Lys  Asp  Ser  Leu  Asn  Lys  Phe  Leu  Phe  Thr  Ile  Pro  Phe  Asp
105                      110                 115                           120

Cys  Trp  Gly  Pro  Val  Lys  Lys
                    125
```

( 2 ) INFORMATION FOR SEQ ID NO: 12:

( i ) SEQUENCE CHARACTERISTICS:
        ( A ) LENGTH: 29 BASES
        ( B ) TYPE: NUCLEIC ACID
        ( C ) STRANDEDNESS: SINGLE
        ( D ) TOPOLOGY: LINEAR ( i i i ) HYPOTHETICAL: NO ( i v ) ANTI-SENSE: NO (x i) SEQUENCE DESCRIPTION: SEQ ID NO: 12:

CGACGGTACC GGCTCCCACC CGCCCACCC 29

(2) INFORMATION FOR SEQ ID NO: 13:

(i) SEQUENCE CHARACTERISTICS:
(A) LENGTH: 40 BASES
(B) TYPE: NUCLEIC ACID
(C) STRANDEDNESS: SINGLE
(D) TOPOLOGY: LINEAR (i i i) HYPOTHETICAL: NO (i v) ANTI-SENSE: YES (x i) SEQUENCE DESCRIPTION: SEQ ID NO: 13:

AGGATCTAGA GGATCCTCAT CACTTTTTGA CTGGCCCCA 40

(2) INFORMATION FOR SEQ ID NO: 14:

(i) SEQUENCE CHARACTERISTICS:
(A) LENGTH: 21 BASES
(B) TYPE: NUCLEIC ACID
(C) STRANDEDNESS: SINGLE
(D) TOPOLOGY: LINEAR (i i i) HYPOTHETICAL: NO (i v) ANTI-SENSE: YES (x i) SEQUENCE DESCRIPTION: SEQ ID NO: 14:

TGGTTCCCAG CAGTCAAAGG G 21

(2) INFORMATION FOR SEQ ID NO: 15:

(i) SEQUENCE CHARACTERISTICS:
(A) LENGTH: 21 BASES
(B) TYPE: NUCLEIC ACID
(C) STRANDEDNESS: SINGLE
(D) TOPOLOGY: LINEAR (i i i) HYPOTHETICAL: NO (i v) ANTI-SENSE: YES (x i) SEQUENCE DESCRIPTION: SEQ ID NO: 15:

ACATCTGCCA TTTCCCCTGC C 21

(2) INFORMATION FOR SEQ ID NO: 16:

(i) SEQUENCE CHARACTERISTICS:
(A) LENGTH: 26 BASES
(B) TYPE: NUCLEIC ACID
(C) STRANDEDNESS: SINGLE
(D) TOPOLOGY: LINEAR (i i i) HYPOTHETICAL: NO (i v) ANTI-SENSE: NO (x i) SEQUENCE DESCRIPTION: SEQ ID NO: 16:

CTATGGAGGT TCCATGTCAG ATAAAG 26

(2) INFORMATION FOR SEQ ID NO: 17:

(i) SEQUENCE CHARACTERISTICS:
(A) LENGTH: 17 BASES
(B) TYPE: NUCLEIC ACID
(C) STRANDEDNESS: SINGLE
(D) TOPOLOGY: LINEAR ( i i i ) HYPOTHETICAL: NO ( i v ) ANTI-SENSE: NO ( x i ) SEQUENCE DESCRIPTION: SEQ ID NO: 17:

ATGTTCATTT GTACCTC                                                17

( 2 ) INFORMATION FOR SEQ ID NO: 18:

( i ) SEQUENCE CHARACTERISTICS:
( A ) LENGTH: 20 BASES
( B ) TYPE: NUCLEIC ACID
( C ) STRANDEDNESS: SINGLE
( D ) TOPOLOGY: LINEAR ( i i i ) HYPOTHETICAL: NO ( i v ) ANTI-SENSE: NO ( x i ) SEQUENCE DESCRIPTION: SEQ ID NO:18:

AGACAGGATC CATCGTACCG                                             20

( 2 ) INFORMATION FOR SEQ ID NO: 19:

( i ) SEQUENCE CHARACTERISTICS:
( A ) LENGTH: 20 BASES
( B ) TYPE: NUCLEIC ACID
( C ) STRANDEDNESS: SINGLE
( D ) TOPOLOGY: LINEAR ( i i i ) HYPOTHETICAL: NO ( i v ) ANTI-SENSE: YES ( x i ) SEQUENCE DESCRIPTION: SEQ ID NO: 19:

CTCATTCAGA AGGAGCAGGC                                             20

( 2 ) INFORMATION FOR SEQ ID NO: 20:

( i ) SEQUENCE CHARACTERISTICS:
( A ) LENGTH: 760
( B ) TYPE: NUCLEIC ACID
( C ) STRANDEDNESS: DOUBLE
( D ) TOPOLOGY: LINEAR ( i i i ) HYPOTHETICAL: NO ( i v ) ANTI-SENSE: NO ( x i ) SEQUENCE DESCRIPTION: SEQ ID NO: 20:

```
GGA  TCCATCGTAC  CGGCCCAAAC  ATG  AGC  AGC  CTC  CCC  CTT  ATG  CAT  CTG  CTC        53
                                   Met  Ser  Ser  Leu  Pro  Leu  Met  His  Leu  Leu
                                                  -20                      -15

CTG  CTG  CTG  CTC  ACA  CTC  CAT  GCT  CCT  CAG  GCA  CAG  GGG  ATG  CCT  ACC      101
Leu  Leu  Leu  Leu  Thr  Leu  His  Ala  Pro  Gln  Ala  Gln  Gly  Met  Pro  Thr
              -10                       -5                       1

ACA  ACA  CTC  CAA  CCT  AAA  AAC  TAC  CTT  GCC  ATG  ATC  CAG  GAA  ATT  ACA      149
Thr  Thr  Leu  Gln  Pro  Lys  Asn  Tyr  Leu  Ala  Met  Ile  Gln  Glu  Ile  Thr
          5                        10                      15

AGA  AGC  CTA  GAG  AAC  CTA  ACT  GTG  ACT  TCA  AAT  AAA  TCC  TTG  ACG  TTG      197
Arg  Ser  Leu  Glu  Asn  Leu  Thr  Val  Thr  Ser  Asn  Lys  Ser  Leu  Thr  Leu
 20                       25                      30                       35

AAT  GAG  CTC  GAA  ACC  CTG  GTG  AAT  AAC  ACT  CTT  CTG  AGA  CCA  AAC  CTG      245
Asn  Glu  Leu  Glu  Thr  Leu  Val  Asn  Asn  Thr  Leu  Leu  Arg  Pro  Asn  Leu
                     40                       45                       50

GAA  GCA  TTC  GTG  ACA  TTT  GCT  GAA  AAC  CAC  TTA  AAA  AAT  ATT  TCA  GGA      293
Glu  Ala  Phe  Val  Thr  Phe  Ala  Glu  Asn  His  Leu  Lys  Asn  Ile  Ser  Gly
```

```
ATC AAG AAA AAC CTT GAG AAA TTC CGG CCA ATC CTG CCC ACG TCT ATG      341
Ile Lys Lys Asn Leu Glu Lys Phe Arg Pro Ile Leu Pro Thr Ser Met
        70                      75                  80

TCC ACG GAA GAG CCA ATC TCT ATT GAG GAG GGC GAC CTT GGT GAT TTC      389
Ser Thr Glu Glu Pro Ile Ser Ile Glu Glu Gly Asp Leu Gly Asp Phe
        85                      90                  95

CGG GCG AAA CTG ATG GAG TAT CTG GTT GTC CTT AGA GAC TCT CTG AAA      437
Arg Ala Lys Leu Met Glu Tyr Leu Val Val Leu Arg Asp Ser Leu Lys
100                     105                 110                 115

CCC ATG ATC ACA GAG CCC TAA AATCTGAAGT GTGAACTCCA GCTCTCTCTC         488
Pro Met Ile Thr Glu Pro
                120

TGGAGCCCTG GAACGTCAGG AACAGCAGAT CGTCCTAAGA TGCGTGGACC GTCTCTCACA    548

CCATCCAGGA CTGACGTTTT CTCCTGTGGA GTCTGTTGAA TTGTTAACTA TCTAATCCCT    608

GAAATGTGCA GCCCCATTTG TCCTTTTGCG ATTAGGTTCT CATTTTTATT GTATTGAGGC    668

TATTTATTTA TGTATGTATT TATTTATTAT CTTGTGCAAT GTGAAATGTA TTTACTTAAC    728

AGAGAAGCCA TGGCCTGCTC CTTCTGAATG AG                                  760
```

(2) INFORMATION FOR SEQ ID NO: 21:

(i) SEQUENCE CHARACTERISTICS:
      (A) LENGTH: 144 AMINO ACIDS
      (B) TYPE: AMINO ACID
      (C) STRANDEDNESS: SINGLE
      (D) TOPOLOGY: LINEAR (iii) HYPOTHETICAL: YES (iv) ANTI-SENSE: NO (xi) SEQUENCE DESCRIPTION: SEQ ID NO: 21:

```
                            Met Ser Ser Leu Pro Leu Met His Leu Leu
                                        -20                 -15

Leu Leu Leu Leu Thr Leu His Ala Pro Gln Ala Gln Gly Met Pro Thr
            -10                 -5                      1

Thr Thr Leu Gln Pro Lys Asn Tyr Leu Ala Met Ile Gln Glu Ile Thr
        5                   10                  15

Arg Ser Leu Glu Asn Leu Thr Val Thr Ser Asn Lys Ser Leu Thr Leu
20                      25                  30                  35

Asn Glu Leu Glu Thr Leu Val Asn Asn Thr Leu Leu Arg Pro Asn Leu
                40                  45                  50

Glu Ala Phe Val Thr Phe Ala Glu Asn His Leu Lys Asn Ile Ser Gly
                55                  60                  65

Ile Lys Lys Asn Leu Glu Lys Phe Arg Pro Ile Leu Pro Thr Ser Met
        70                      75                  80

Ser Thr Glu Glu Pro Ile Ser Ile Glu Glu Gly Asp Leu Gly Asp Phe
        85                      90                  95

Arg Ala Lys Leu Met Glu Tyr Leu Val Val Leu Arg Asp Ser Leu Lys
100                     105                 110                 115

Pro Met Ile Thr Glu Pro
                120
```

(2) INFORMATION FOR SEQ ID NO: 22:

(i) SEQUENCE CHARACTERISTICS:
      (A) LENGTH: 29 BASES
      (B) TYPE: NUCLEIC ACID
      (C) STRANDEDNESS: SINGLE

-continued (D) TOPOLOGY: LINEAR (iii) HYPOTHETICAL: NO (iv) ANTI-SENSE: NO (xi) SEQUENCE DESCRIPTION: SEQ ID NO: 22:

GGGGAATTCA TATGCCTACC ACAACACTC    29

(2) INFORMATION FOR SEQ ID NO:23:

(i) SEQUENCE CHARACTERISTICS:
(A) LENGTH: 38 BASES
(B) TYPE: NUCLEIC ACID
(C) STRANDEDNESS: SINGLE
(D) TOPOLOGY: LINEAR (iii) HYPOTHETICAL: NO (iv) ANTI-SENSE: YES (xi) SEQUENCE DESCRIPTION: SEQ ID NO: 23:

CCCAAGCTTG GATCCTATTA GGGCTCTGTG ATCATGGG    38

(2) INFORMATION FOR SEQ ID NO:24:

(i) SEQUENCE CHARACTERISTICS:
(A) LENGTH: 21 BASES
(B) TYPE: NUCLEIC ACID
(C) STRANDEDNESS: SINGLE
(D) TOPOLOGY: LINEAR (iii) HYPOTHETICAL: NO (iv) ANTI-SENSE: NO (xi) SEQUENCE DESCRIPTION: SEQ ID NO: 24:

AGGATGTGGC TGCAGAACCT G    21